United States Patent
Schibli et al.

(10) Patent No.: US 10,357,576 B2
(45) Date of Patent: Jul. 23, 2019

(54) 18F-LABELLED FOLATE/ANTIFOLATE ANALOGUES

(71) Applicant: MERCK & CIE, Schaffhausen (CH)

(72) Inventors: Roger Schibli, Baden (CH); Rudolf Moser, Schaffhausen (CH); Cristina Magdalena Mueller, Nussbaumen (CH); Simon Mensah Ametamey, Zurich (CH); Thomas Betzel, Hofheim am Taunus (DE); Viola Groehn, Dachsen (CH)

(73) Assignee: MERECK & CIE, Schaffhusen (CH)

( * ) Notice: Subject to any disclaimer, the term of this patent is extended or adjusted under 35 U.S.C. 154(b) by 688 days.

(21) Appl. No.: 14/399,688

(22) PCT Filed: May 8, 2013

(86) PCT No.: PCT/EP2013/059584
§ 371 (c)(1),
(2) Date: Nov. 7, 2014

(87) PCT Pub. No.: WO2013/167653
PCT Pub. Date: Nov. 14, 2013

(65) Prior Publication Data
US 2015/0125390 A1 May 7, 2015

(30) Foreign Application Priority Data

May 8, 2012 (EP) .................... 12167126

(51) Int. Cl.
| | | |
|---|---|---|
| A61K 51/00 | (2006.01) |
| A61M 36/14 | (2006.01) |
| A61K 51/04 | (2006.01) |
| C07B 59/00 | (2006.01) |
| C07D 475/04 | (2006.01) |
| G01N 33/60 | (2006.01) |

(52) U.S. Cl.
CPC ........ *A61K 51/0459* (2013.01); *C07B 59/002* (2013.01); *C07D 475/04* (2013.01); *G01N 33/60* (2013.01); *G01N 2333/705* (2013.01)

(58) Field of Classification Search
CPC .............. G01N 33/60; G01N 2333/705; C07B 59/002; C07D 475/04
USPC ........................................................ 424/1.85
See application file for complete search history.

(56) References Cited

U.S. PATENT DOCUMENTS

2010/0005653 A1    3/2010    Ametamey et al.

FOREIGN PATENT DOCUMENTS

WO        2008125617 A2        10/2008
WO    WO 2008125617 A2 *    10/2008    ......... A61K 51/0459

OTHER PUBLICATIONS

Lasne et al. Top. Curr. Med. Chem. 2002, 201-258.*

(Continued)

*Primary Examiner* — Michael G. Hartley
*Assistant Examiner* — Sean R Donohue
(74) *Attorney, Agent, or Firm* — Millen White Zelano and Branigan, PC; Csaba Henter

(57) ABSTRACT

The present invention is directed towards new $^{18}$F-folate/antifolate analog radiopharmaceuticals, wherein the phenyl group within folate structures has been replaced by an $^{18}$F-heterocycle, their precursors, a method of their preparation, as well as their use in diagnosis of a cell or population of cells expressing a folate-receptor and monitoring of cancer and inflammatory and autoimmune diseases and therapy thereof.

13 Claims, 10 Drawing Sheets

(56) References Cited

OTHER PUBLICATIONS

Yamini et al. E-Journal of Chemistry, 2008, 263-270.*
International Search Report for PCT/EP2013/059584 dated Jun. 17, 2013.
Roberts, E. C. et al., "Folic acid analogs. Modifications in the benzene-ring region. 1. 2'-and 3'-Azafolic acids," Journal of Medicinal Chemistry, Feb. 1, 1971, vol. 14, No. 2, pp. 125-130.
Roberts, E. C. et al., "Folic acid analogs. Modifications in the benzene-ring region. 5. 2', 6'-diazafolic acid," Journal of Heterocyclic Chemistry, Aug. 1, 1974, pp. 547-550.
Roberts, E. C. et al., "Folic acid analogs. Modifications in the benzene-ring region. 2. Thiazole analogs," Journal of Medicinal Chemistry, Dec. 1, 1972, vol. 15, No. 12, pp. 1310-1312.
Nakahara, Yu-Uji et al., "Synthesis of N-([2-([(2-amino-3, 4-dihydro-4-oxo-6-pteridinyl)methyl]amino)-5-pyrazinyl] carbonyl)-L-glutamic acid(2',5'-diazafolic acid)" Journal of Heterocyclic Chemistry, Jan. 1, 1975, pp. 1073-1074.
Gossett, L. S. et al., "The synthesis and biological activity of a series of 2,4-diaminopyridol [2,3-d]pyrimidine based antifolates as antineoplastic and antiarthritic agents," Bioorganic & Medicinal Chemistry Letters, Jan. 1, 1999, vol. 9, No. 1, pp. 75-78.
Ross, T. L. et al., "A new 18F-labeled folic acid derivatives with improved properties for the PET Imaging of folate receptor-positive tumors," The Journal of Nuclear Medicine, Nov. 1, 2010, vol. 541, No. 11, pp. 1756-1762.
Ross, T. L. et al., "Fluorine-18 Click Radiosynthesis and Preclinical Evaluation of a New 18 F-Labeled Folic Acid Derivatives," Bioconjugate Chemistry, Dec. 17, 2008, vol. 19, No. 12, pp. 2462-2470.
Miller et al., "Imaging Atherosclerotic Plaque Inflammation via Folate Receptor Targeting Using a Novel 18 F-Folate Radiotracer", Research Article, MOlecular Imaging, vol. 13, 2014, pp. 1-11.
Betzel et al., "Radiosynthesis and Preclinical Evaluation of 1'-Aza-2'-[18F]fluorofolic Acid: A Novel PET Radiotracer for Folate Receptor Targeting", Bioconjugate Chemistry, ACS Publications, 2012 American Chemical Society, pp. 205-214.
Cristina Muller, "Folate-Based Radiotracers for PET Imaging-Update and Perspectives", Open Access Molecules 2013, 18, pp. 5005-5031.

* cited by examiner

18F-LABELLED FOLATE/ANTIFOLATE ANALOGUES

FIELD OF INVENTION

The present invention is directed towards new $^{18}$F-folate/antifolate analogue radiopharmaceuticals, wherein the phenyl group within a folate structure, has been replaced by an $^{18}$F-heterocycle, their precursors, a method of their preparation, as well as their use in diagnosis of a cell or population of cells expressing a folate-receptor and monitoring of cancer and inflammatory and autoimmune diseases and therapy thereof.

BACKGROUND

Cell-specific targeting for delivery of effector moieties such as diagnostic or therapeutic agents is a widely researched field and has led to the development of non-invasive diagnostic and/or therapeutic medical applications. In particular in the field of nuclear medicine procedures and treatments, which employ radioactive materials emitting electromagnetic radiations as γ rays or particle emitting radiation, selective localization of these radioactive materials in targeted cells or tissues is required to achieve either high signal intensity for visualization of specific tissues, assessing a disease and/or monitoring effects of therapeutic treatments, or high radiation dose, for delivering adequate doses of ionizing radiation to a specified diseased site, without the risk of radiation injury/radiotoxicity in other e.g. healthy tissues. It is thus of crucial interest to determine and assess cell-specific structures and in particular structures that are present in case of cancer (i.e. tumors) or inflammatory and autoimmune diseases, such as receptors, antigens, haptens and the like which can be specifically targeted by the respective biological vehicles.

The folate receptor (FR) has been identified as one of these structures (Low, Acc Chem Res. 2008; 41:120-9). The FR is a high-affinity ($K_D < 10^{-9}$ M) membrane-associated protein. In normal tissues and organs FR-expression is highly restricted to only a few organs (e.g. kidney, lungs, choroids plexus, and placenta), where it largely occurs at the luminal surface of epithelial cells and is therefore not accessible for folate in the circulation. The FR-alpha is frequently overexpressed on a wide variety of specific cell types, such as epithelial tumors (e.g. ovarian, cervical, endometrial, breast, colorectal, kidney, lung, see e.g. Parker et al., Anal. Biochem. 2005; 2:284-293), whereas the FR-beta is frequently overexpressed in leukaemia cells (approx. 70% of acute myelogenous leukaemia (AML) are FR-beta positive). Both may therefore be used as a valuable tumor marker for selective tumor-targeting (Elnakat and Ratnam, Adv. Drug Deliv. Rev. 2004; 56:1067-84). In addition it has recently been discovered that activated (but not resting) synovial macrophages in patients diagnosed with rheumatoid arthritis possess a functionally active FR-beta (Nakashima-Matsushita et al, Arthritis & Rheumatism, 1999, 42(8): 1609-16). Therefore activated macrophages can be selectively targeted with folate conjugates in arthritic joints, a capability that opens possibilities for the diagnosis and treatment of rheumatoid arthritis (Paulos et al, Adv. Drug Deliv. Rev. 2004; 56:1205-17). Other inflammatory pathologies in which folate receptor positive macrophages are commonly enriched include rheumatoid arthritis, Crohn's disease, atherosclerosis, sarcoidosis, glomerulonephritis, osteoarthritis, organ transplant rejection, ulcerative colitis, Sjogren's syndrome, diabetes, ischemia/reperfusion injury, impact trauma, microbial infection, prosthesis osteolysis, liver steatosis, and multiple sclerosis (Piscaer et al. 2011, Arthritis & Rheumatism 63, 1898; Henne et al. 2012, Mol Pharm, 9:1435-40; Ayala-Lopez et al. 2010, J Nucl Med 51, 768). Folate-targeted therapeutic agents offer great promise for the development of highly potent, nontoxic treatment modalities for the same diseases (Hansen M. J et al., Targeted Drug Strategies for Cancer and Inflammation, Springer Science+Business Media, 2011, 181-193). FR-beta is also overexpressed on tumor-associated macrophages (TAMs). TAMs show mostly pro-tumoral functions, promoting tumor cell survival, proliferation, and dissemination. Clinical studies have shown a correlation between the numbers of TAMs and poor prognosis for amongst others breast, prostate, ovarian, cervical, endometrial, esophageal, pancreatic, glioblastoma and bladder cancers (Kurahara H. et al., Ann Surg Oncol., 2012 Feb. 16, Nagai T. et al., Cancer Immunol Immunother (2009) 581577-1586, Puig-Kroeger A. et al. Cancer Res 2009; 69 (24). Dec. 15, 2009, Turk M. J. et al., Cancer Letters 213 (2004) 165-172). Therefore tumor-associated macrophages can be selectively targeted with folate conjugates. That opens possibilities for the diagnosis and treatment of cancer.

Another such cell-specific structure is the proton-coupled folate transporter (PCFT). PCFT is expressed in the proximal small intestine, where it mediates folate absorption at acidic pH (Qiu et al, Cell. 2006 Dec. 1; 127(5):917-28) and in tissues such as liver and kidney, which do not experience low pH conditions (Zhao et al., Expert Rev Mol Med. 2009 Jan. 28; 11:e4). The interstitial pH of solid tumors is often acidic (Helmlinger et al., Nat Med. 1997 February; 3(2): 177-82; Raghunand et al., Biochem Pharmacol. 1999 Feb. 1; 57(3):309-12), which favors PCFT transport. A prominent low-pH transport route was identified in 29 of 32 solid human tumor cell lines (Zhao et al., Clin Cancer Res. 2004 Jan. 15; 10(2):718-27), and high levels of human PCFT (hPCFT) transcripts were reported in a broad range of human tumors (Kugel Desmoulin et al., Am Assoc Cancer Res 51:1103). The role of hPCFT in antifolate activity and tumor selectivity is still evolving. Transport of classic antifolates by PCFT has been described previously (Zhao et al., Mol Pharmacol. 2008 September; 74(3):854-62. Epub 2008 Jun. 4). A targeting agent of the proton-coupled folate transporter opens possibilities for the diagnosis and treatment of tumors.

Folates and its derivatives have thus been intensively studied over the past 15 years as targeting agents for the delivery of therapeutic and/or diagnostic agents to cell populations bearing folate receptors in order to achieve a selective accumulation of therapeutic and/or diagnostic agents in such cells relative to normal cells.

Various probes have been conjugated to folic acid and (pre)clinically evaluated, including folate radiopharmaceuticals (Leamon and Low, Drug Discov. Today 2001; 6:44-51 and Jammaz et al, J. Label Compd. Radiopharm. 2006; 49:125-137; Müller & Schibli, 2011 J. Nucl. Med. 52, 1; Müller, Current Pharm Design, 2012), folate-conjugates of chemotherapeutic agents (Leamon and Reddy, Adv. Drug Deliv. Rev. 2004; 56:1127-41; Leamon et al, Bioconjugate Chem. 2005; 16:803-11), proteins and protein toxins (Ward et al, J. Drug Target. 2000; 8:119-23; Leamon et al, J. Biol. Chem. 1993; 268:24847-54; Leamon and Low, J. Drug Target. 1994; 2:101-12), antisense oliconucleotides (Li et al, Pharm. Res. 1998; 15:1540-45; Zhao and Lee, Adv. Drug Deliv. Rev. 2004; 56:1193-204), liposomes (Lee and Low, Biochim. Biophys. Acta-Biomembr. 1995; 1233:134-44; Gabizon et al, Adv. Drug Deliv. Rev. 2004; 56:1177-92), hapten molecules (Paulos et al, Adv. Drug Deliv. Rev. 2004; 56:1205-17), MRI contrast agents (Konda et al, Magn. Reson. Mat. Phys. Biol. Med. 2001; 12:104-13) etc.

Folate radiopharmaceuticals can be in particular very useful for an improved diagnosis and evaluation of the effectiveness of cancer therapy. This may include assessment and/or prediction of a treatment response and consequently improvement of radiation dosimetry. A typical visualization technique is positron emission tomography (PET), whereby a positron emitting radionuclide is administered to a subject, and as it undergoes radioactive decay the gamma rays resulting from the positron annihilation are detected in the PET scanner. Due to its high sensitivity and well-elaborated quantification methods, PET has established itself as one of the most sophisticated functional imaging technologies to assess regional uptake and affinity of ligands or metabolic substrates in brain and other organs and thus provides measures of imaging based on metabolic activity. Suitable radiopharmaceuticals for PET may be based on a metal isotope in combination with a chelator for entrapment of the metal (e.g. $^{68}$Ga, $^{64}$Cu, $^{89}$Zr), or on a covalently linked isotope, typically positron emitting isotopes with short half lives such as $^{11}$C (ca. 20 min), $^{13}$N (ca. 10 min), $^{15}$O (ca. 2 min) and $^{18}$F (ca. 110 min).

Over the past decades, a number of chelate-based folate radiopharmaceuticals, in particular $^{111}$In-, $^{99m}$Tc- and $^{67/8}$Ga$^{8}$Ga-derivatives, have been synthesized and successfully evaluated as diagnostic agents for imaging folate receptor-positive tumors using SPECT or PET (see e.g. Siegel et al., J. Nucl. Med. 2003, 44:700; Müller et al., J. Organomet. Chem. 2004, 689:4712; Mathias et al., Nucl. Med. Biol. 2003, 30(7):725; WO 2008/125618; Müller et al. 2011, Nucl. Med. & Biol. 38, 715).

More recently, folate radiopharmaceuticals carrying a covalently linked positron emitting 18F nuclide have been reported (see e.g. Bettio et al., J. Nucl. Med., 2006, 47(7), 1153; WO 2006/071754; WO 2008/098112; WO 2008/125613; WO 2008/125615; WO 2008/125617; WO 2010/040854; Ross et al. 2010, J Nucl. Med., 51, 1756; Fischer et al. 2012, Bioconjug. Chem.), and shown to be most suitable for PET imaging because of its excellent imaging characteristics which would fulfill all of the above mentioned considerations.

Yet, while known 18F folate radiopharmaceuticals show promising results, there is still a need for compounds that show high FR-specificity and are suitable for routine clinical applications and yet can be obtained in efficient and versatile ways with high radiochemical yields Applicants have now found that folate derivatives wherein the phenyl group of the folate skeleton has been replaced by a heterocycle can be substituted with one or more 18F nuclides in versatile and efficient ways and high radiochemical yields. The obtained 18F-folate/antifolate analogue compounds show high selectivity for FR-positive tissue and thus it can be concluded such modifications to the folate skeleton exert no negative effect on folate receptor binding affinity.

Thus, the present invention is directed to new $^{18}$F-folate/antifolate analogue radiopharmaceuticals, wherein the phenyl group, which connects the condensed pyrimidine heterocycle via suitable linkers (such as a —CH$_2$—NH-linker at the C6 position of a pteridine heterocycle) to the amino acid portion within folate structures, has been replaced by an 18F-substituted 5- or 6-membered heterocycle, their precursors, a method of their preparation, as well as their use in diagnosis of a cell or population of cells expressing a folate-receptor and monitoring of cancer and inflammatory and autoimmune diseases and therapy thereof.

SUMMARY OF THE INVENTION

The present invention is in a first aspect directed to new $^{18}$F-folate/antifolate analogue radiopharmaceuticals and precursors thereof (hereinafter also called compounds of the invention), wherein the phenyl group, which connects the condensed pyrimidine heterocycle to the amino acid portion has been replaced by an $^{18}$F-substituted 5- or 6-membered heterocycle.

More specifically, the present invention is directed towards compounds of formula I,

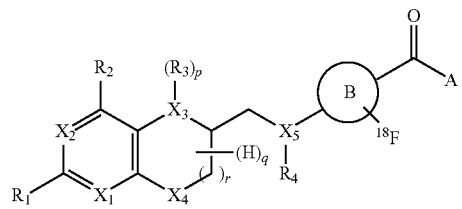

wherein

A is an amino acid,

B is a 5- or 6-membered heterocyclic ring comprising at least one heteroatom independently selected from N, O and S, $X_1$ to $X_5$ are independently of each other N or C, $R_1$, $R_2$ are independently of each other H, Hal, —OR$_7$, —NR$_8$R$_9$, C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein R$_7$ is H or C1-C6 alkyl and R$_8$, R$_9$ are independently of each other selected from H, formyl, straight chain or branched C1-C12 alkyl, which is unsubstituted or substituted by at least one CN, Hal, or NO$_2$, and wherein one or more of embedded, non-adjacent CH$_2$ groups may independently be replaced by —O—, —CO—, —CO—O—, —CO—NR'—, —CH=CH—, —C≡C—, wherein R' is H, C1-C6 alkyl, $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, p is 0, 1 or 2, q has a value of 1 to 7, and r is 0 or 1.

Even more specifically, the present invention is directed towards compounds of formula I wherein the 5- or 6-membered heterocyclic ring is a 5-membered heterocyclic ring with at least one nitrogen, oxygen or sulphur atom, as represented by formula Ia, or wherein the 5- or 6-membered heterocyclic ring is a 6-membered heterocyclic ring with at least one nitrogen, oxygen or sulphur atom, as represented by formula Ib.

Thus, in specific embodiments, the present invention is directed towards compounds of formula Ia and Ib

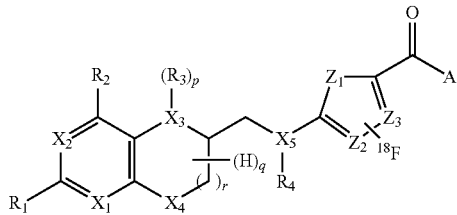

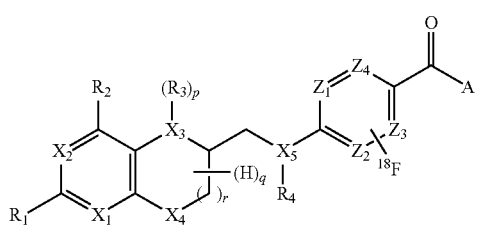

wherein
A is an amino acid,
$Z_1$ to $Z_4$ are independently of each other N, O, S or C, with the proviso that in formula Ia at least one of $Z_1$ and $Z_4$ is N, O or S and in formula Ib at least one of $Z_1$, $Z_2$ and $Z_3$ is N, O or S, $X_1$ to $X_5$ are independently of each other N or C, $R_1$, $R_2$ are independently of each other H, Hal, —$OR_7$, —$NR_8R_9$, C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein $R_7$ is H or C1-C6 alkyl and $R_8$, $R_9$ are independently of each other selected from H, formyl, straight chain or branched C1-C12 alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H, C1-C6 alkyl, $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, p is 0, 1 or 2,
q has a value of 1 to 7, and
r is 0 or 1.

In some embodiments, the present invention is directed towards compounds of formula I or more specifically formula Ia, wherein the 5-membered heterocyclic ring is a pyrrole or pyrrolidine, a furan or tetrahydrofuran, or a thiophene or tetrahydrothiophene, i.e. wherein either (a) $Z_1$ is N, O, or S and $Z_2$, $Z_3$ are C or (b) $Z_2$ is N, O or S and $Z_1$, $Z_3$ are C; or (c) $Z_3$ is N, O or S and $Z_1$, $Z_2$ are C; or wherein the 5-membered heterocyclic ring is an imidazole or imidazolidine, or a dioxolane, or a 1,3-dithiolane, i.e. wherein either (d) $Z_1$, $Z_2$ are both N, O or S and $Z_3$ is C or (e) $Z_1$, $Z_3$ are both either N, O, or S and $Z_2$ is C; or wherein the 5-membered heterocyclic ring is a pyrazole or pyrazolidine or a 1,2-dithiolane, i.e wherein (f) $Z_2$, $Z_3$ are both either N or S and $Z_1$ is C; or wherein the 5-membered heterocyclic ring is an oxazole or oxazolidine, or a thiazole or thiazolidine, i.e. wherein either (g) one of $Z_1$ and $Z_2$ is N and one of $Z_1$ and $Z_2$ is O or S and $Z_3$ is C or (h) one of $Z_1$ and $Z_3$ is N and one of $Z_1$ and $Z_3$ is O or S and $Z_2$ is C; or wherein the 5-membered heterocyclic ring is an isoxazole or isoxazolidine, or an isothiazole or isothiazolidine, i.e wherein (i) one of $Z_2$ and $Z_3$ is N and one of $Z_2$ and $Z_3$ is O or S and $Z_1$ is C; or wherein the 5-membered heterocyclic ring is a triazole or a oxadiazole or a thiadiazole, i.e. wherein (j) $Z_1$, $Z_2$, $Z_2$ are all N, or (k) $Z_1$ is O or S and $Z_2$, $Z_3$ are both N.

In other embodiments, the present invention is directed towards compounds of formula I wherein the 5- or 6-membered heterocyclic ring is a 6-membered ring with at least one nitrogen atom (herein also referred to as an aza-heterocycle), represented by formula Ib,

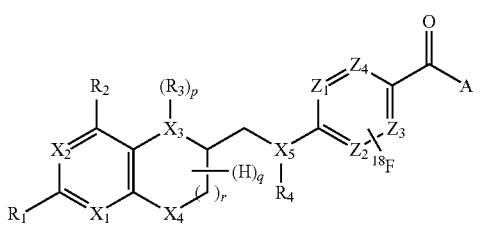

wherein
A is an amino acid,
$Z_1$ to $Z_4$ are independently of each other N or C, with the proviso that at least one of $Z_1$ and $Z_4$ is N, $X_1$ to $X_5$ are independently of each other N or C, $R_1$, $R_2$ are independently of each other H, Hal, —$OR_7$, —$NR_8R_9$, C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein $R_7$ is H or C1-C6 alkyl and $R_8$, $R_9$ are independently of each other selected from H, formyl, straight chain or branched C1-C12 alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H, C1-C6 alkyl, $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, p is 0, 1 or 2,
q has a value of 1 to 7, and
r is 0 or 1.

For use in the present invention, such an aza-heterocycle is a pyridine, a diazine or a triazine. Thus, in preferred embodiments, the present invention is directed towards compounds of formula I or more specifically formula Ib, wherein (a) $Z_1$ is N and $Z_2$, $Z_3$, $Z_4$ are C or (b) $Z_4$ is N and $Z_1$, $Z_2$, $Z_3$ are C or (c) $Z_1$, $Z_2$ are N and $Z_3$, $Z_4$ are C or (d) $Z_1$, $Z_3$ are N and $Z_2$, $Z_4$ are C or (e) $Z_1$, $Z_4$ are N and $Z_2$, $Z_3$ are C or (f) $Z_3$, $Z_4$ are N and $Z_1$, $Z_2$ are C or (g) $Z_1$, $Z_2$, $Z_3$ are N and $Z_4$ is C or (h) $Z_1$, $Z_3$, $Z_4$ are N and $Z_2$ is C.

In a further aspect the present invention is directed to a method of their preparation. In a preferred embodiment the $^{18}$F-folate/antifolate analogue radiopharmaceuticals of the invention are obtained through direct $^{18}$F-radiolabeling of suitable precursors (and subsequent deprotection steps).

In another aspect the present invention is directed to the use in diagnosis of a cell or population of cells expressing a folate-receptor and monitoring of cancer and cancer therapy in vitro or in vivo or monitoring of inflammatory and autoimmune diseases such rheumatoid arthritis and therapy thereof.

In one embodiment, the present invention is directed towards uses of $^{18}$F-folate/antifolate analogue radiopharmaceuticals of the invention for diagnostic imaging of a cell or population of cells expressing a folate-receptor.

More specifically the present invention includes methods for diagnostic imaging of a cell or population of cells expressing a folate-receptor, which includes for example methods for in vitro detection of a cell expressing the folate receptor, for example a tumor cell or an activated macrophage, in a tissue sample. Such methods may also be performed in vivo.

Thus, in a further embodiment the present invention is directed towards uses of $^{18}$F-folate/antifolate analogue radiopharmaceuticals of the invention for convenient and effective administration to a subject in need for diagnostic imaging and/or monitoring of cancer or inflammatory and autoimmune disease therapy. The subject of the methods of the present invention is preferably a mammal, such as an animal or a human, preferably a human.

Such methods of the invention may be performed in combination with any other methods of diagnosis or therapy of cancer or inflammatory and autoimmune diseases including methods using other already developed diagnostic and/or therapeutic agents and utilizing x-ray computed tomography (CT), magnetic resonance imaging (MRI), functional magnetic resonance imaging (fMRI), single photon emission computed tomography (SPECT), optical imaging, and ultrasound.

Other features and advantages of the invention will be apparent from the following detailed description thereof and from the claims.

DETAILED DESCRIPTION OF THE INVENTION

Figure 1A:
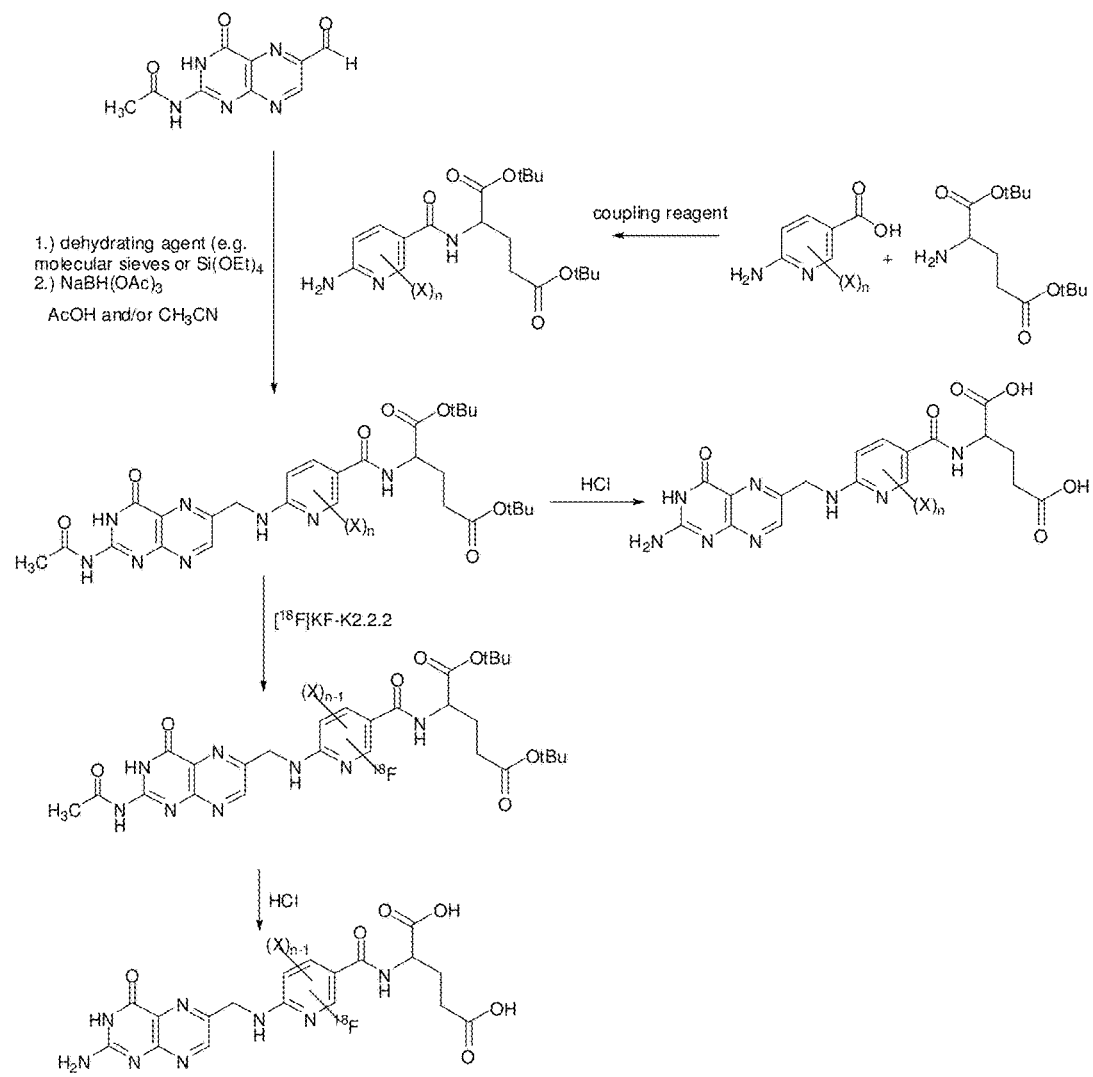
FIG. 1A, 1B, 1C. Representative synthesis schemes for the preparation of $^{18}$F-substituted 3'-aza-folic acid with $(X)_n$-substituted 6-aminonicotinic acid as the heterocycle. $(X)_n$ represents one or more electron withdrawing substituents for introduction of $^{18}$F, e.g. CL, Br, NO$_2$, F.
Figure 1B:
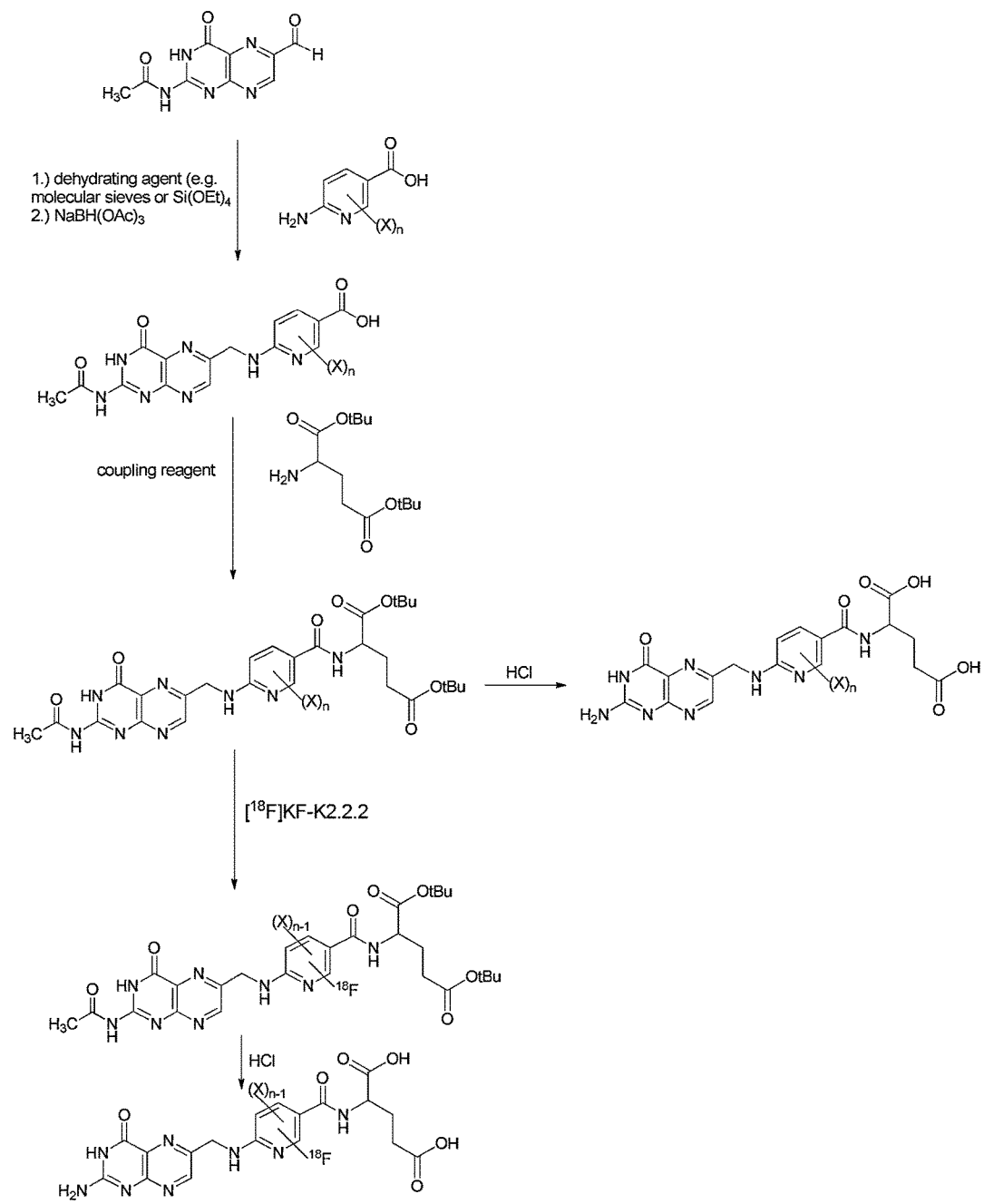
Figure 1C:
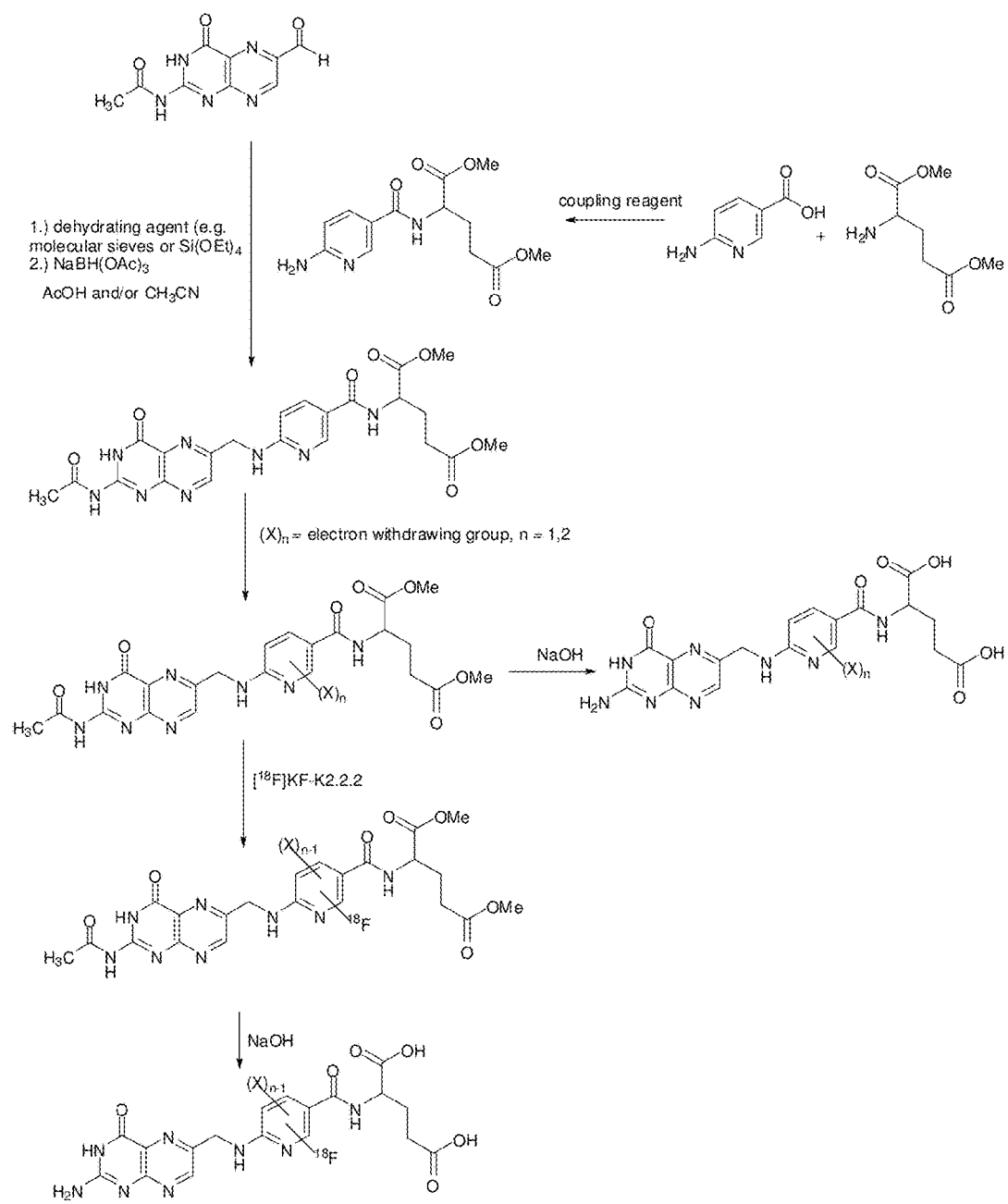
Figure 1D:
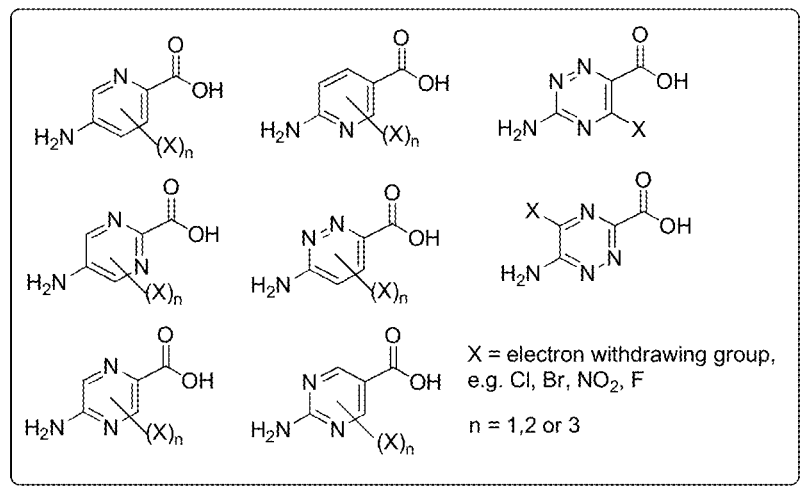
FIG. 1D. Selection of aza-, diaza- or triazaheterocycles to be used as alternatives for the $(X)_n$-substituted 6-aminonicotinic acid used in the synthetic schemes of FIGS. 1A, 1B, 1C. $(X)_n$ represents one or more electron withdrawing substituents, e.g. CL, Br, NO$_2$, F.

The present invention is in a first aspect directed to new $^{18}$F-folate/antifolate analogue radiopharmaceuticals (hereinafter also called compounds of the invention) and precursors thereof, wherein the phenyl group, which connects the condensed pyrimidine heterocycle to the amino acid portion has been replaced by an $^{18}$F-substituted 5- or 6-membered heterocycle.

Folate/antifolate analogues for use in the present invention are folate/antifolate compounds wherein the phenyl group of the folate skeleton, i.e. in folates the phenyl group of the aminobenzoyl group linking the condensed pyrimidine heterocycle to the amino acid (or glutamic acid) portion has been replaced by a 5- or 6-membered heterocyclic ring comprising at least one heteroatom independently selected from O, N and S.

The term heterocycle as used for the folate/antifolate structures herein refers to a saturated or (partially) unsaturated heterocycle carrying one or more N, O or S atoms, more specifically 1, 2 or 3 N, O or S-atoms. Thus typical N, O, or S-heterocycles include e.g. pyridine, a diazine or triazine, more specifically pyridine, pyrimidine, pyridazine, pyrazine or triazine, tetrahydrofuran, furan, thiolanes, thiophene, pyrrolidine, pyrrole, thiazolidine, isothiazolidine, thiazole, isothiazole, oxazolidine, isoxazolidine, oxazole, isoxazole, pyrazolidine, imidazolidine, pyrazole, imidazole, dioxolane, dithiazole, thiadiazole, oxadiazole, furazan or triazole. The N, O or S-heterocycle is preferably 1,4-linked (or para-position) in case of 6-membered rings and 1,3-linked in case of 5-membered rings in case of 6-membered heterocyclic rings N-heterocycles, i.e. a saturated or (partially) unsaturated heterocycle carrying 1, 2 or 3 N-atoms are preferred, and is typically linked in para-position through an amino-linker to a condensed pyrimidine heterocycle unit (or derivatives thereof) and through a carbonyl group to one or more amino acid units to obtain an aza-folate and derivatives thereof according to the invention. As used herein a "condensed pyrimidine heterocycle" includes a pyrimidine fused with a further 5- or 6-membered heterocycle, such as a pteridine or a pyrrolopyrimidine bicycle. As used herein the term "amino acid" includes compounds with both an amino group (e.g., NH$_2$ or NH$_3^+$) and a carboxylic acid group (e.g., COOH or COO$^-$). In a specific embodiment, the amino acid may be an α-amino acid, a β-amino acid, a D-amino acid or a L-amino acid. The amino acid may be a naturally occurring amino acid (e.g., alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine, or histidine, etc.) or it may be a derivative thereof. Examples of derivatives include optionally substituted amino acids, e.g. having one or more substituents selected from CN, Hal, and/or NO$_2$ (e.g. fluoroglutamic acid). The amino acid may also include any other non-naturally occurring amino acids, such as e.g. norleucine, norvaline, L- or D-naphthalanine, ornithine, homoarginine and others well known in the peptide art (see for example in M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, both of which are incorporated herein by reference). Amino acids and amino acid analogs/derivatives can be purchased commercially (Sigma Chemical Co.; Advanced Chemtech) or synthesized using methods known in the art. In another specific embodiment, the amino acid may also be part of a polyamino acid (also termed polypeptide), wherein a plurality of same or different amino acids as defined hereinabove are covalently linked, i.e. linked through conventional peptide or other bonds. Preferred amino acids include for example glutamic acid, aspartic acid, glutamine, aspartine, lysine, arginine, cystein, and derivatives thereof and preferred polyamino acids include homopolymers the respective homopolymers thereof (i.e. polyglutamic acid, polyaspartic acid, etc). Most preferred are optionally substituted aspartic and glutamic acid.

It is understood that derivatives of an $^{18}F$-folate/antifolate compound of the invention may include further variations in the pyrimidine heterocycle unit and/or the nature of the one or more amino acids, including a different oxidation state of the pteridine ring (of the pyrazine heterocycle) to obtain more reduced forms such as a dihydro-folate or a tetrahydro-folate, as well as the type of the one carbon substituent at N5 and/or N10 positions, the type and number of conjugated amino acid residues, the substitution pattern of the various units, and other derivatives.

As indicated hereinabove, in case of $^{18}F$-folate/antifolate compounds of the invention carrying a 6-membered heterocycle N-heterocycles (also called aza-folates) are preferred. Preferred representatives of such aza-folates as used herein are based on an aza-folate skeleton, i.e. N-[4[[(2-amino-1,4-dihydro-4-oxo-6-pteridinyl)methyl]amino]-azaheterocycloyl-]-glutamic acid, wherein azaheterocycloyl refers to 2'- or 3'-pyridinyl derivatives thereof, and includes optionally substituted aza-folic acid, aza-folinic acid, pteropoly-glutamic acid, and folate receptor-binding pteridines such as tetrahydropterins, dihydro-aza-folates, tetrahydro-aza-folates, and their known deaza- and dideaza-pteroyl analogs.

In analogy, preferred representatives of 18F-folate/antifolate analogues comprising a 5-membered heterocyclic ring as defined hereinabove instead of the azaheterocycloyl group are the 2-thienyl-, 1,3,4-thiadiazol-2-yl-, 4-thiazolyl-, 2-thiazolyl-, 5-thiazolyl-, 1H-pyrazol-3-yl-, 1H-imidazol-5-yl, 1H-pyrrol-2-yl-, 1H-pyrrol-3-yl-, and 2-furanyl-compounds.

The aza-folate structure is the preferred basic structure used for the compounds of this invention. The expression "deaza- and dideaza-pteroyl analogs" refers to the art recognized pteroyl-analogs wherein one or two nitrogen atoms of four nitrogen atoms in the pteroylgroup have been substituted by a carbon atom substituted for one or two nitrogen atoms. For example, the deaza analogs include the 1-deaza, 3-deaza, 5-deaza, 8-deaza, and 10-deaza analogs. The dideaza analogs include, for example, 1,5-dideaza, 5,10-dideaza, 8,10-dideaza, and 5,8-dideaza analogs. Known and preferred deaza analogs, in which the phenyl group can be substituted with an aza-heterocycle to arrive at the corresponding aza-folate derivative include N-[4-[2-[(6R)-2-amino-1,4,5,6,7,8-hexahydro-4-oxopyrido[2,3-d]pyrimidin-6-yl]ethyl]benzoyl]-L-glutamic acid (Lometrexol) and N-[4-[1-[(2,4-diamino-6-pteridinyl)methyl]propyl]benzoyl]-L-glutamic acid (Edatrexate).

In a particular embodiment, the new folate/antifolate analogue radiopharmaceuticals are compounds of formula I,

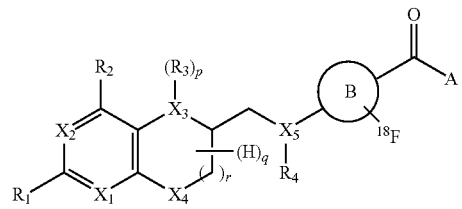

wherein
A is an amino acid,
B is a 5- or 6-membered heterocyclic ring comprising at least one heteroatom independently selected from N, O and S,
$X_1$ to $X_5$ are independently of each other N or C,
$R_1$, $R_2$ are independently of each other H, Hal, —$OR_7$, —$NR_8R_9$, C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein $R_7$ is H or C1-C6 alkyl and $R_8$, $R_9$ are independently of each other selected from H, formyl, straight chain or branched C1-C12 alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H, C1-C6 alkyl,
$R_3$, $R_4$ are independently of each other H, formyl, iminomethyl, nitroso, C1-C12 alkyl, C1-C12 alkoxy, C1-C12 alkanoyl, halosubstituted C1-C12 alkanoyl,
p is 0, 1 or 2,
q has a value of 1 to 7, and
r is 0 or 1.

In one preferred embodiment, the present invention is directed towards compounds of formula I wherein the 5- or 6-membered heterocyclic ring is a 5-membered heterocycle with at least one nitrogen, oxygen or sulphur atom, as represented by formula Ia,

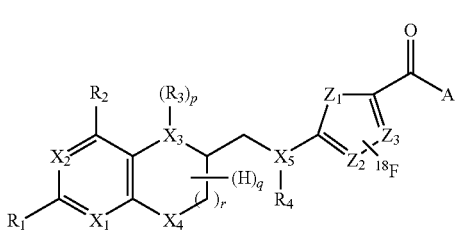

wherein
A is an amino acid,
$Z_1$ to $Z_3$ are independently of each other N, O, S or C, with the proviso that at least one of $Z_1$, $Z_2$ and $Z_3$ is N, O or S,
$X_1$ to $X_5$ are independently of each other N or C,
$R_1$, $R_2$ are independently of each other H, Hal, —$OR_7$, —$NR_8R_9$, C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein $R_7$ is H or C1-C6 alkyl and $R_8$, $R_9$ are independently of each other selected from H, formyl, straight chain or branched C1-C12 alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H, C1-C6 alkyl, R$_3$, R$_4$ are independently of each other H, formyl, iminomethyl, nitroso, C1-C12 alkyl, C1-C12 alkoxy, C1-C12 alkanoyl, halosubstituted C1-C12 alkanoyl, p is 0, 1 or 2, q has a value of 1 to 7, and r is 0 or 1.

In preferred embodiments, the 5-membered heterocyclic ring is a pyrrol or pyrrolidine, a furan or tetrahydrofuran, or a thiophen or tetrahydrothiophen, i.e. wherein either (a) $Z_1$ is N, O, or S and $Z_2$, $Z_3$ are C or (b) $Z_2$ is N, O or S and $Z_1$, $Z_3$ are C; or (C) $Z_3$ is N, O or S and $Z_1$, $Z_2$ are C; or the 5-membered heterocyclic ring is an imidazole or imidazolidine, or a dioxolane, or a 1,3-dithiolane, i.e. wherein either (d) $Z_1$, $Z_2$ are both N, O or S and $Z_3$ is C or (e) $Z_1$, $Z_3$ are both either N, O, or S and $Z_2$ is C; or the 5-membered heterocyclic ring is a pyrazole or pyrazolidine or a 1,2-dithiolane, i.e wherein (f) $Z_2$, $Z_3$ are both either N or S and $Z_1$ is C; or the 5-membered heterocyclic ring is an oxazole or oxazolidine, or a thiazole or thiazolidine, i.e. wherein either (g) one of $Z_1$ and $Z_2$ is N and one of $Z_1$ and $Z_2$ is O or S and $Z_3$ is C or (h) one of $Z_1$ and $Z_3$ is N and one of $Z_1$ and $Z_3$ is O or S and $Z_2$ is C; or the 5-membered heterocyclic ring is an isoxazole or isoxazolidine, or an isothiazole or isothiazolidine, i.e wherein (i) one of $Z_2$ and $Z_3$ is N and one of $Z_2$ and $Z_3$ is O or S and $Z_1$ is C; or the 5-membered heterocyclic ring is a triazole or a oxadiazole or a thiadiazole, i.e. wherein (j) $Z_1$, $Z_2$, $Z_2$ are all N, or (k) $Z_1$ is O or S and $Z_2$, $Z_3$ are both N.

In another preferred embodiment, the present invention is directed towards compounds of formula I wherein the 5- or 6-membered heterocyclic ring is a 6-membered heterocyclic ring with at least one nitrogen, oxygen or sulphur atom, preferably at least one nitrogen atom, represented by formula Ib,

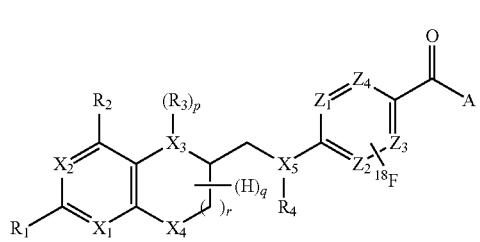

wherein

A is an amino acid, $Z_1$ to $Z_4$ are independently of each other N or C, with the proviso that at least one of $Z_1$ and $Z_4$ is N, $X_1$ to $X_5$ are independently of each other N or C, R$_1$, R$_2$ are independently of each other H, Hal, —OR$_7$, —NR$_8$R$_9$, C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein R$_7$ is H or C1-C6 alkyl and R$_8$, R$_9$ are independently of each other selected from H, formyl, straight chain or branched C1-C12 alkyl, which is unsubstituted or substituted by at least one CN, Hal, or NO$_2$, and wherein one or more of embedded, non-adjacent CH$_2$ groups may independently be replaced by —O—, —CO—, —CO—O—, —CO—NR'—, —CH=CH—, —C≡C—, wherein R' is H, C1-C6 alkyl, R$_3$, R$_4$ are independently of each other H, formyl, iminomethyl, nitroso, C1-C12 alkyl, C1-C12 alkoxy, C1-C12 alkanoyl, halosubstituted C1-C12 alkanoyl, p is 0, 1 or 2, q has a value of 1 to 7, and r is 0 or 1.

As defined hereinabove, such an aza-heterocycle is a pyridine, a diazine or a triazine. Thus, in specific embodiments, the present invention is directed towards compounds of formula I, wherein (a) $Z_1$ is N and $Z_2$, $Z_3$, $Z_4$ are C or (b) $Z_4$ is N and $Z_1$, $Z_2$, $Z_3$ are C or (c) $Z_1$, $Z_2$ are N and $Z_3$, $Z_4$ are C or (d) $Z_1$, $Z_3$ are N and $Z_2$, $Z_4$ are C or (e) $Z_1$, $Z_4$ are N and $Z_2$, $Z_3$ are C or (f) $Z_3$, $Z_4$ are N and $Z_1$, $Z_2$ are C or (g) $Z_1$, $Z_2$, $Z_3$ are N and $Z_4$ is C or (h) $Z_1$, $Z_3$, $Z_4$ are N and $Z_2$ is C.

Thus the present invention is in particular directed towards compounds of formula I having a pyridine group as an aza-heterocycle, i.e. wherein Z1 is N as represented by formula II or wherein Z4 is N as represented by formula III

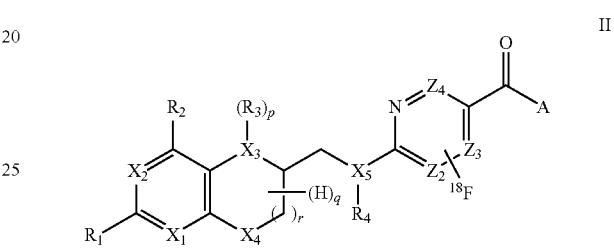

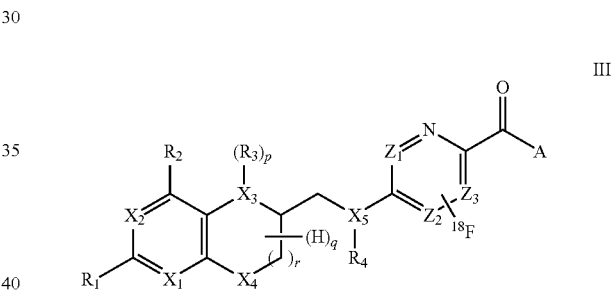

wherein

A is an amino acid, $Z_1$ to $Z_4$ are independently of each other N or C, $X_1$ to $X_5$ are independently of each other N or C, R$_1$, R$_2$ are independently of each other H, Hal, —OR$_7$, —NR$_8$R$_9$, C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein R$_7$ is H or C1-C6 alkyl and R$_8$, R$_9$ are independently of each other selected from H, formyl, straight chain or branched C1-C12 alkyl, which is unsubstituted or substituted by at least one CN, Hal, or NO$_2$, and wherein one or more of embedded, non-adjacent CH$_2$ groups may independently be replaced by —O—, —CO—, —CO—O—, —CO—NR'—, —CH=CH—, —C≡C—, wherein R' is H, C1-C6 alkyl, R$_3$, R$_4$ are independently of each other H, formyl, iminomethyl, nitroso, C1-C12 alkyl, C1-C12 alkoxy, C1-C12 alkanoyl, halosubstituted C1-C12 alkanoyl, p is 0, 1 or 2, q has a value of 1 to 7, and r is 0 or 1.

More specifically, the present invention is further directed towards compounds of formulas I to III wherein A is e.g. a glutamic acid residue, represented by formula IVa or IVb, IVa

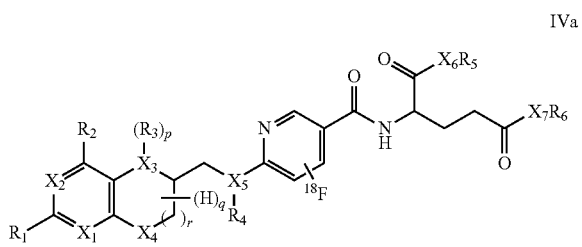

IVb

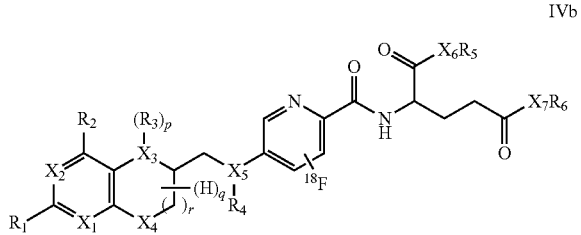

IVd

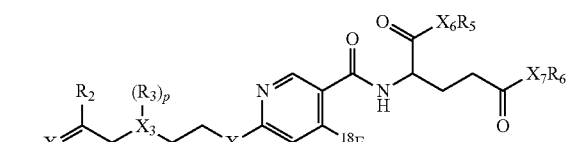

IVe

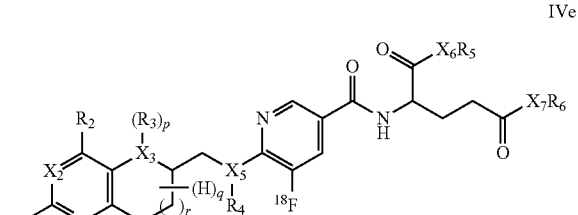

wherein $X_1$ to $X_5$ are independently of each other N or C, $X_6$, $X_7$ are independently of each other C, N or O, $R_1$, $R_2$ are independently of each other H, Hal, —$OR_7$, —$NR_8R_9$, C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein $R_7$ is H or C1-C6 alkyl and $R_8$, $R_9$ are independently of each other selected from H, formyl, straight chain or branched C1-C12 alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H, C1-C6 alkyl, $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, $R_5$, $R_6$ are independently of each other H or straight chain or branched C1-C12 alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H, C1-C6 alkyl, p is 0, 1 or 2, q has a value of 1 to 7, and r is 0 or 1.

Preferred embodiments of compounds of formula IVa and IVb include compounds of formulas IVc, IVd and IVe, IVc

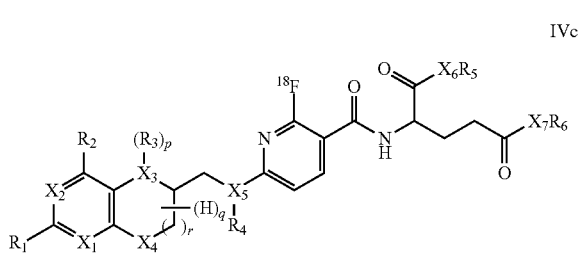

wherein $X_1$ to $X_7$, $R_1$ to $R_9$, R', n, p, q and r are defined as hereinabove.

Especially preferred embodiments of compounds of formulae IVa to IVe include compounds, wherein e.g. $X_1$ to $X_5$ are N, $R_1$ is $NH_2$, $R_2$ is O, $R_3$ and $R_4$ are both H, p is 0 and q is 1.

Thus, in a further specific embodiment the present invention is directed to a compound of formulas IVf and IVg IVf

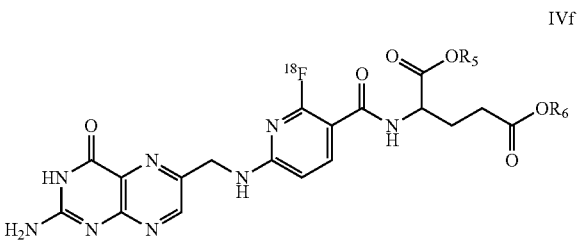

IVg

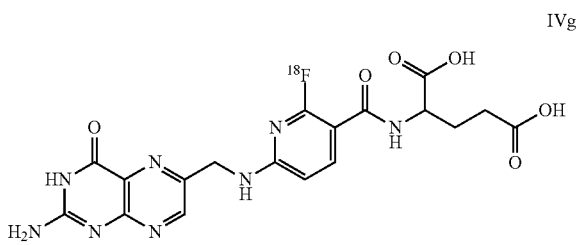

wherein $R_5$, $R_6$ are independently of each other H or straight chain or branched C1-C12 alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H, C1-C6 alkyl.

Further embodiments compounds of formula I to III include compounds wherein the aza-heterocycle is a diazine having formula Va, Vb, Vc, Vd,

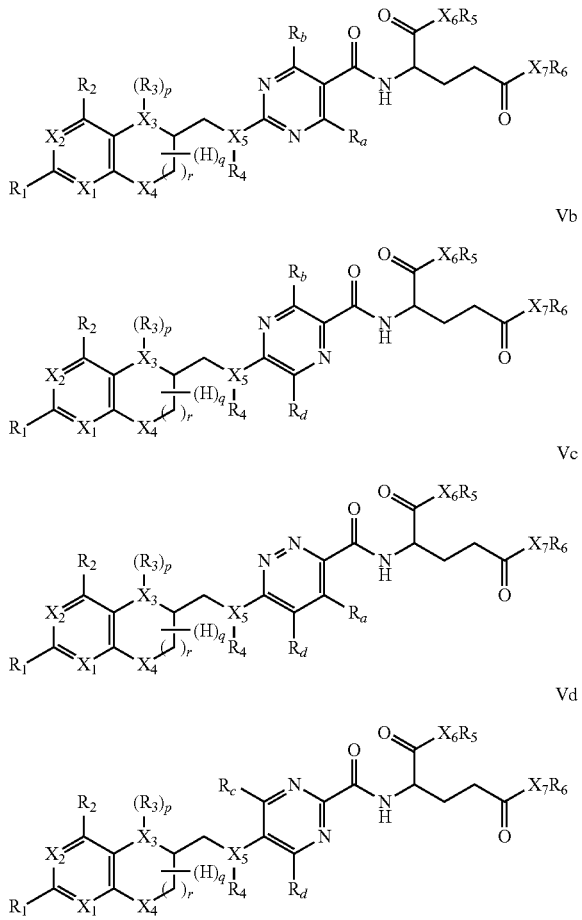

Va

Vb

Vc

Vd wherein $X_1$ to $X_5$ are independently of each other N or C, $X_6$, $X_7$ are independently of each other C, N or O, $R_a$, $R_b$, $R_c$, $R_d$ are independently of each other H or $^{18}F$, with the proviso that one of $R_a$, $R_b$, $R_c$, $R_d$ is $^{18}F$, $R_1$, $R_2$ are independently of each other H, Hal, —$OR_7$, —$NR_8R_9$, C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein $R_7$ is H or C1-C6 alkyl and $R_8$, $R_9$ are independently of each other selected from H, formyl, straight chain or branched C1-C12 alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H, C1-C6 alkyl, $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, $R_5$, $R_6$ are independently of each other H or straight chain or branched C1-C12 alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H, C1-C6 alkyl, p is 0, 1 or 2, q has a value of 1 to 7, and r is 0 or 1.

Yet further embodiments compounds of formula I to III include compounds wherein the aza-heterocycle is a triazine having formula VIa, VIb,

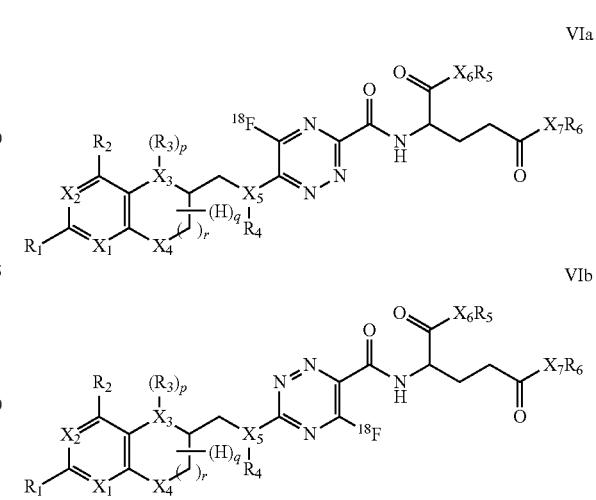

VIa

VIb wherein $X_1$ to $X_5$ are independently of each other N or C, $X_6$, $X_7$ are independently of each other C, N or O, $R_1$, $R_2$ are independently of each other H, Hal, —$OR_7$, —$NR_8R_9$, C1-C12 alkyl, C1-C12 alkoxy, C1-C12 alkanoyl, C2-C12 alkenyl, C2-C12 alkynyl, (C1-C12 alkoxy)carbonyl, and (C1-C12 alkylamino)carbonyl, wherein $R_7$ is H or C1-C6 alkyl and $R_8$, $R_9$ are independently of each other selected from H, formyl, straight chain or branched C1-C12 alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H, C1-C6 alkyl, $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, $R_5$, $R_6$ are independently of each other H or straight chain or branched C1-C12 alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H, C1-C6 alkyl, p is 0, 1 or 2, q has a value of 1 to 7, and r is 0 or 1.

In further specific embodiments groups $R_3$, $R_4$ as they appear in all compounds of the invention are preferably independently of each other H, formyl, iminomethyl, nitroso, C1-C12 alkyl, C1-C12 alkoxy, C1-C12 alkanoyl, halosubstituted C1-C12 alkanoyl. More preferably groups $R_3$, $R_4$ are independently of each other H, methyl or formyl.

In further specific embodiments the groups $R_5$, $R_6$ as they appear in all compounds of the invention are preferably independently of each other H or straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H, C1-C6 alkyl.

More preferably groups $R_5$, $R_6$ are independently of each other H, methyl, ethyl or tert.-butyl.

It is understood, that the abbreviations "N" and "C" are representative for all possible degrees of saturation, i.e. N includes —NH— and —N= linkages and C includes —CH$_2$— and —CH= linkages.

It is further understood, that (H)$_q$ represents all H substituents on the indicated ring (i.e. on $X_3$, C6, C7 and $X_4$). For example q=5 for a fully saturated unsubstituted analog ($X_3$=$X_4$=N, p=0) or q=7 for a fully saturated unsubstituted 5,8-dideaza analog ($X_3$=$X_4$=C, p=0) and q=1 for a fully unsaturated analog with $X_3$=$X_4$=N, p=0.

Preferred embodiments of compounds of formulae I to III include compounds, wherein e.g. $X_1$ to $X_5$ are N, $R_1$ is N$Y_1Y_2$, $R_2$ is O, p is 1 and q is 3.

Thus, in a further specific embodiment the present invention is directed to a compound of formulas VII and VIII,

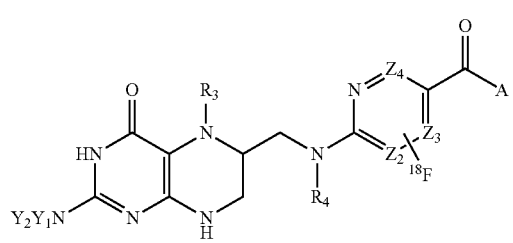

VII

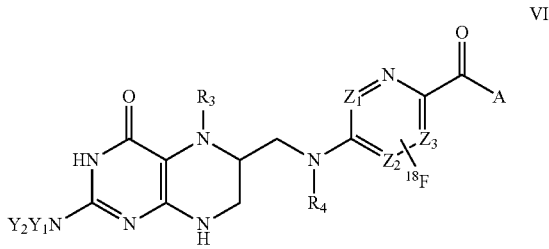

VIII wherein
A is an amino acid,
$Z_1$ to $Z_4$ are independently of each other N or C,
$R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, and
$Y_1$, $Y_2$ are independently of each other selected from H, formyl, straight chain or branched C1-C12 alkyl, which is unsubstituted or substituted by at least one CN, Hal, or NO$_2$, and wherein one or more of embedded, non-adjacent CH$_2$ groups may independently be replaced by —O—, —CO—, —CO—O—, —CO—NR'—, —CH=CH—, —C≡C—, wherein R' is H or C1-C6 alkyl.

Specific embodiments of compounds VII and VIII include compounds of formulas IXa, IXb, IXc, IXd, IXe, IXf

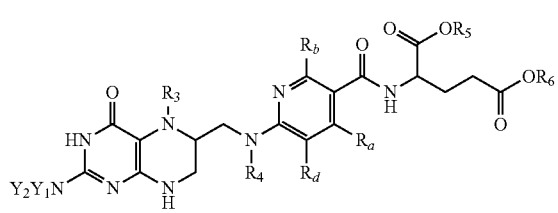

IXa

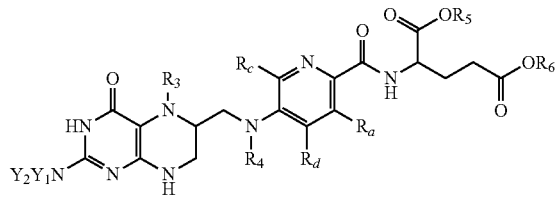

IXb

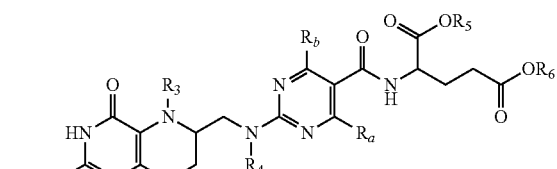

IXc

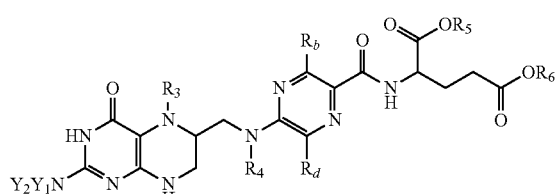

IXd

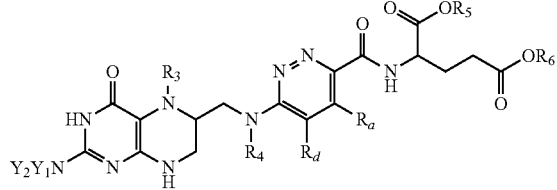

IXe

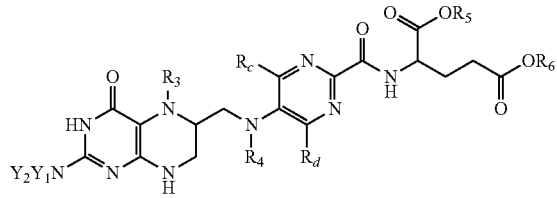

IXf wherein
$R_a$, $R_b$, $R_c$, $R_d$ are independently of each other $^{18}$F or H, with the proviso that one of $R_a$, $R_b$, $R_c$, $R_d$ is $^{18}$F,
$R_3$, $R_4$ are independently of each other H, formyl, iminomethyl, nitroso, C1-C12 alkyl, C1-C12 alkoxy, C1-C12 alkanoyl, halosubstituted C1-C12 alkanoyl,
$R_5$, $R_6$ are independently of each other H or straight chain or branched C1-C12 alkyl, which is unsubstituted or substituted by at least one CN, Hal, or NO$_2$, and wherein one or more of embedded, non-adjacent CH$_2$ groups may independently be replaced by —O—, —CO—, —CO—O—, —CO—NR'—, —CH=CH—, —C≡C—, wherein R' is H or C1-C6 alkyl, and
$Y_1$, $Y_2$ are independently of each other selected from H, formyl, straight chain or branched $C_1$-$C_{12}$ alkyl, which is unsubstituted or substituted by at least one CN, Hal, or NO$_2$, and wherein one or more of embedded, non-adjacent CH$_2$ groups may independently be replaced by —O—, —CO—, —CO—O—, —CO—NR'—, —CH=CH—, —C≡C—, wherein R' is H or C1-C6 alkyl.

Preferred embodiments of compounds of formulae I to III also include compounds, wherein e.g. $X_1$ to $X_5$ are N, $R_1$ is $NY_1Y_2$, $R_2$ is O, p is 0 and q is 1.

Thus, in a further specific embodiment the present invention is directed to a compound of formulas X and XI,

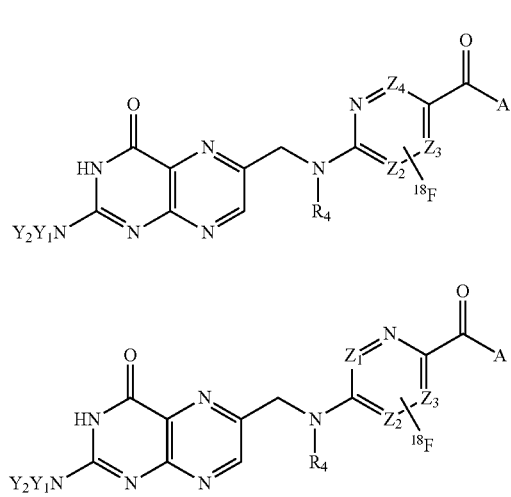

wherein

A is an amino acid, $Z_1$ to $Z_4$ are independently of each other N or C, $R_4$ is H, formyl, iminomethyl, nitroso, C1-C12 alkyl, C1-C12 alkoxy, C1-C12 alkanoyl, halosubstituted C1-C12 alkanoyl, and $Y_1$, $Y_2$ are independently of each other selected from H, formyl, straight chain or branched C1-C12 alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or C1-C6 alkyl.

Specific embodiments of compounds X and XI include compounds of formulas XIIa, XIIb, XIIc, XIId, XIIe, XIIf

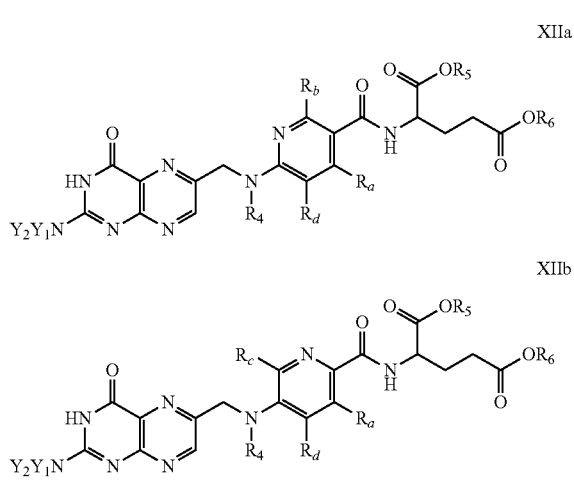

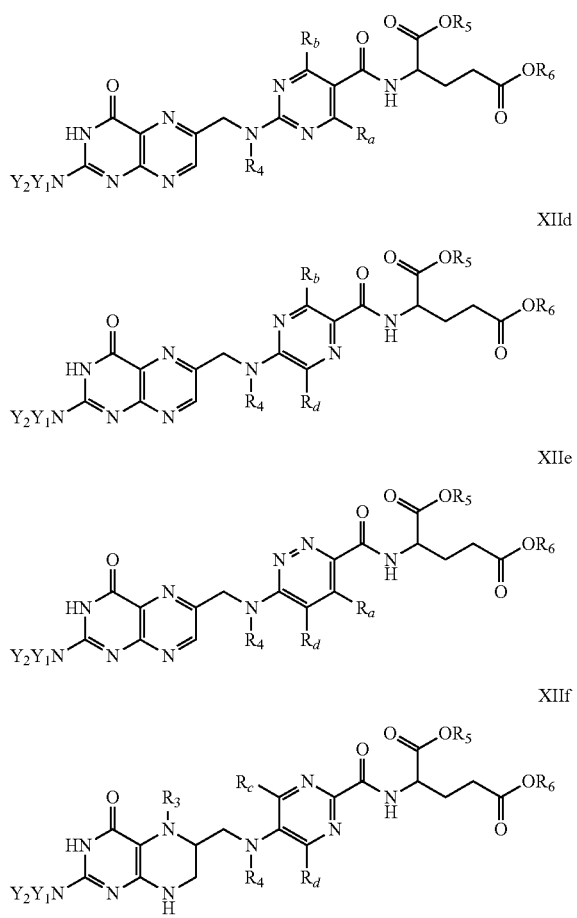

wherein $R_a$, $R_b$, $R_c$, $R_d$ are independently of each other $^{18}F$ or H, with the proviso that one of $R_a$, $R_b$, $R_c$, $R_d$ is $^{18}F$, $R_3$, $R_4$ are independently of each other H, formyl, iminomethyl, nitroso, C1-C12 alkyl, C1-C12 alkoxy, C1-C12 alkanoyl, halosubstituted C1-C12 alkanoyl, $R_5$, $R_6$ are independently of each other H or straight chain or branched C1-C12 alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or C1-C6 alkyl, and $Y_1$, $Y_2$ are independently of each other selected from H, formyl, straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or C1-C6 alkyl.

Other embodiments are compounds of formula I to III wherein $X_1$ to $X_5$ are N, $R_1$ and $R_2$ are $NH_2$, $R_3$ is H, $R_4$ is $CH_3$, p is 0, and q is 1.

Thus, in a further specific embodiment the present invention is directed to a compound of formulas XIII and IVX,

XIII

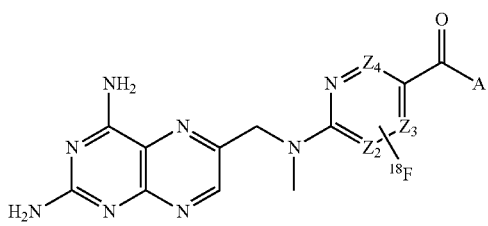

IVX

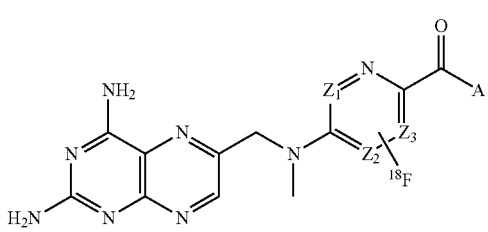

wherein

A is an amino acid, and $Z_1$ to $Z_4$ are independently of each other N or C,

Specific embodiments of compounds XIII and IVX include compounds of formulas XVa, XVb, XVc, XVd, XVe, XVf XVa

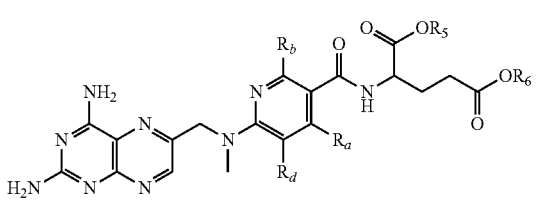

XVb

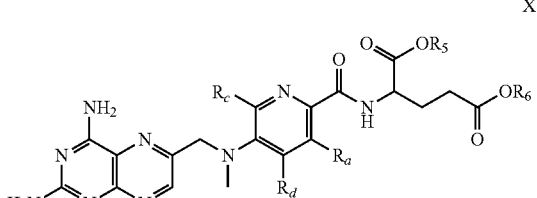

XVc

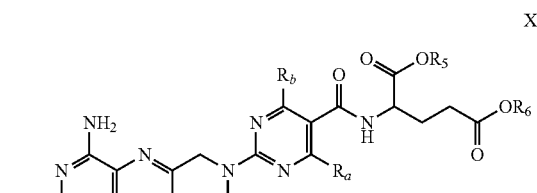

XVd

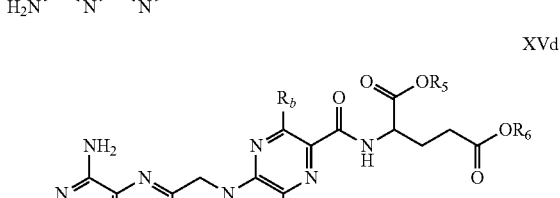

XVe

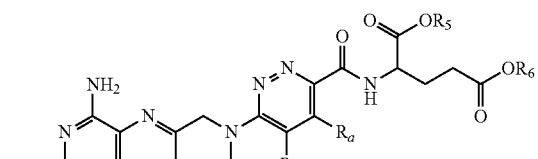

XVf

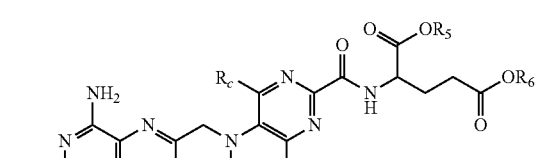

wherein $R_a$, $R_b$, $R_c$, $R_d$ are independently of each other $^{18}$F or H, with the proviso that one of $R_a$, $R_b$, $R_c$, $R_d$ is $^{18}$F, and $R_5$, $R_6$ are independently of each other H or straight chain or branched C1-C12 alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or C1-C6 alkyl.

Other embodiments are compounds of formulae I to III wherein $X_1$ to $X_5$ and $R_1$ and $R_2$ are N, $R_4$=$R_5$=$R_6$ is H, $R_3$ is $CH_3$ or formyl, p is 1 and q is 4.

Thus, in a further specific embodiment the present invention is directed to a compound of formula XVI and XVII,

XVI

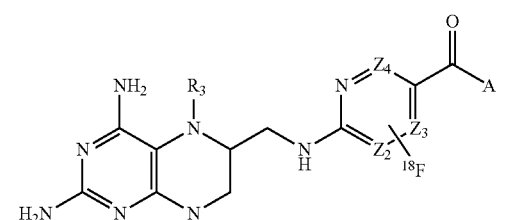

XVII

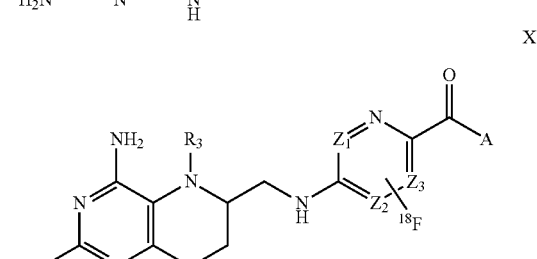

wherein

A is an amino acid, $Z_1$ to $Z_4$ are independently of each other N or C, and $R_3$ is H, methyl- or formyl-.

Specific embodiments of compounds XVI and XVII include compounds of formulas XVIIIa, XVIIIb, XVIIIc, XVIIId, XVIIIe, XVIIIf

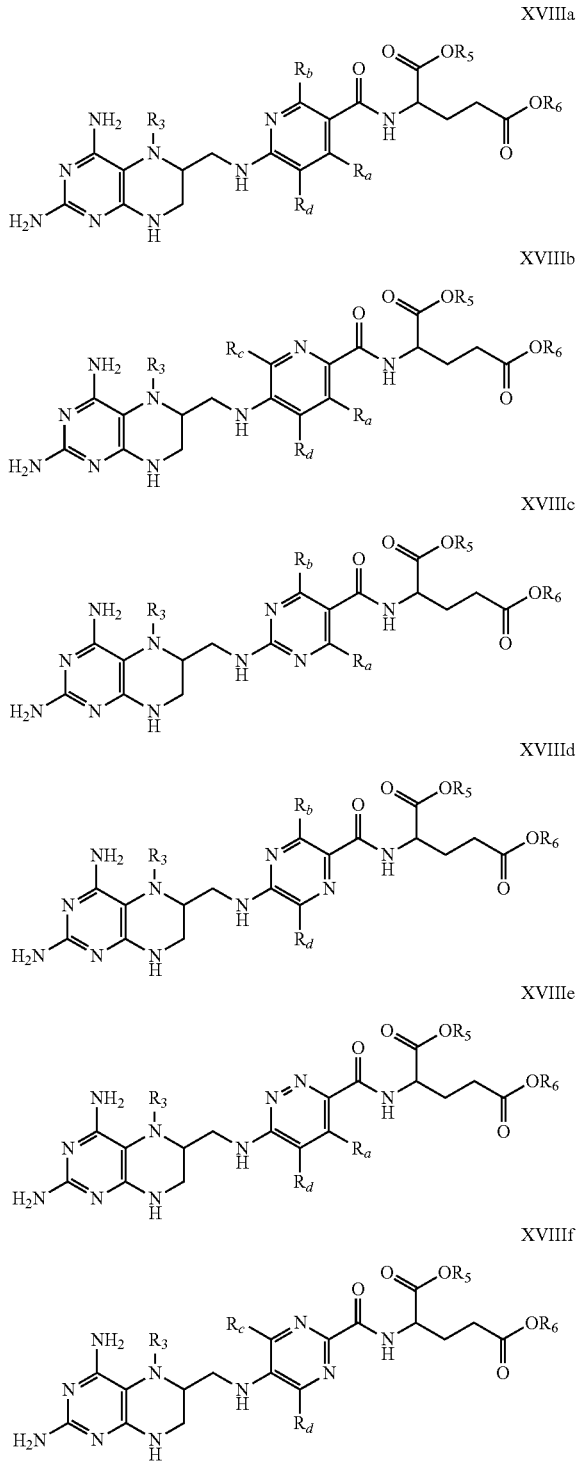

XVIIIa
XVIIIb
XVIIIc
XVIIId
XVIIIe
XVIIIf wherein $R_a$, $R_b$, $R_c$, $R_d$ are independently of each other $^{18}F$ or H, with the proviso that one of $R_a$, $R_b$, $R_c$, $R_d$ is $^{18}F$, $R_3$ is H, methyl- or formyl-, and $R_5$, $R_6$ are independently of each other H or straight chain or branched $C_1$-$C_{12}$ alkyl, which is unsubstituted or substituted by at least one CN, Hal, or $NO_2$, and wherein one or more of embedded, non-adjacent $CH_2$ groups may independently be replaced by —O—, —CO—, —CO—O—, —CO—NR'—, —CH=CH—, —C≡C—, wherein R' is H or C1-C6 alkyl.

The term "alkyl", when used singly or in combination, refers to straight chain or branched alkyl groups containing in the indicted number of C-atoms, typically containing 1 to 12, preferably 1 to 8 more preferably 1 to 4 carbon atoms, such as methyl, ethyl, propyl, isopropyl, butyl, sec-butyl, isobutyl, t-butyl, pentyl isopentyl, neopentyl, hexyl and the like.

As used herein, the term "alkenyl" (i.e. an alkyl group as defined above having at least one double bond), singly or in combination with other groups, refers to straight chain or branched alkylene groups containing 2 to 12 carbon atoms, such as methylene, ethylene, propylene, isopropylene, butylene, t-butylene, sec-butylene, isobutylene, amylene, isoamylene, pentylene, isopentylene, hexylene and the like. The preferred alkenyl groups contain 2 to 8 carbon atoms.

The term "alkynyl" (i.e. an alkyl group as defined above having at least one triple bond) as used herein refers to a linear or branched chain of carbon atoms with one or more carbon-carbon triple bonds. The preferred alkynyl groups contain 2 to 12, more preferably 2 to 8 carbon atoms.

The term "alkoxy" as used herein refers to an alkyl, as defined above, substituted with oxygen, such as methoxy, ethoxy, propoxy, isopropoxy, butoxy, tert-butoxy and the like.

The term "alkanoyl" as used herein refers to formyl, or an alkyl, as defined above, terminally-substituted with a carbonyl such as acetyl, propanoyl, butanoyl, pentanoyl and the like.

The term "alkylamino" as used herein refers to an alkyl, as defined above, substituted with nitrogen, including both monoalkylamino such as methylamino, ethylamino, propylamino, tert-butylamino, and the like, and dialkylamino such as dimethylamino, diethylamino, methylpropylamino, and the like.

The term "halo" as used herein refers to any Group 17 element and includes fluoro, chloro, bromo, iodo, and astatine(o).

The expression "optionally substituted" preferably includes substitution with hydroxy, alkoxy, (di)alkylamino, alkylsulfonyl, alkylcarbonyl, alkylcarbonyloxy, alkoxycarbonyl, carboxyl, Hal, CN, $NO_2$.

In a preferred embodiment $R_1$ and $R_2$ are independently of each other H, —OR", —NHR" wherein R" is H, C1-C6 alkyl, C1-C4 alkoxy, C1-C4 alkanoyl, (C1-C4 alkoxy)carbonyl, and (C1-C6 alkylamino)carbonyl, more preferably $R_1$ and $R_2$ are independently of each other —OH, $NH_2$.

In a preferred embodiment $R_3$ and $R_4$ are independently of each other H, methyl or formyl.

In a preferred embodiment $R_5$ and $R_6$ are independently of each other H, methyl, ethyl or tert.-butyl.

In a preferred embodiment R' is H, methyl or ethyl.
In a preferred embodiment $R_7$ is H, methyl or ethyl.
In a preferred embodiment $R_8$ is H, methyl or ethyl.
In a preferred embodiment $Y_1$ and $Y_2$ are independently of each other H, methyl or ethyl.

In a further aspect the present invention provides a method of synthesizing a compound of the invention. Applicants have found that the folate radiopharmaceuticals of the invention may be obtained through direct radiolabeling with [$^{18}F$]fluoride.

The $^{18}F$ nuclide is usually available as electrophilic [$^{18}F$]$F_2$ and as generally used herein, as nucleophilic [$^{18}F$] fluoride. In form of [$^{18}F$]fluoride fluorine-18 is producible more efficiently. In addition, this is the only possibility for preparing no carrier added radiotracers sufficiently.

Thus, in specific embodiment a method of production of the invention comprises the steps of providing a precursor which is an azafolate carrying a substituent amenable to substitution by a [$^{18}$F]fluoride, and reacting said precursor with [$^{18}$F]fluoride activated by phase transfer catalysts such as tetrabutylammonium carbonate or aminopolyethers (e.g. Kryptofix© 2.2.2) in combination with potassium carbonate or oxalate to form a compound of the invention.

Typically, a substituent amenable to substitution by a [$^{18}$F]fluoride, is an electron-withdrawing group which can act as a leaving group and thus can be exchanged by an incoming [$^{18}$F]fluoride or else can act as an activator for the introduction of the [$^{18}$F]fluoride. Suitable electron-withdrawing groups include —NO$_2$, —CN, —SO$_3$R', —COOR', —COR', —F, —Cl, —Br. The expression "carbocyclic and heterocyclic group comprising five-, six- or ten-membered ring systems and the like" preferably includes phenyl, naphthyl, azetidinyl, pyrrolidinyl, imidazolyl, indolyl, oxadiazolyl, thiadiazolyl, triazolyl, tetrazolyl, oxatriazolyl, thiatriazolyl, pyridazinyl, morpholinyl, pyrimidinyl, pyrazinyl, pyridyl, quinolinyl, isoquinolinyl, piperidinyl, pyrazolyl, imidazopyridinyl and piperazinyl, more preferably phenyl, naphthyl, pyrrolidinyl, imidazolyl, triazolyl, pyrimidinyl, pyridyl, piperidinyl, and pyrazolyl, most preferably phenyl, pyridyl and naphthyl.

Thus, in a preferred embodiment the folate radiopharmaceuticals were obtained in a direct labeling method based on a $^{18}$F-for-nitro- or $^{18}$F-for-chloro-exchange.

In a typical reaction, the precursor is dissolved in a suitable organic solvent was added to dry $^{18}$F-Fluoride-cryptate. The resulting mixture was heated to an appropriate temperature and a suitable reaction time e.g. around 160° C. for 10 min. After short cartridge purification, deprotection was carried out under basic or acidic conditions and a gentle heating for 10 min. Crude product solution was neutralized and injected to semi-prep HPLC system. The radioactive product was collected and the HPLC solvents removed by another solid phase extraction or by a stream of nitrogen, vacuum and gentle heating. For the formulation, the dry product was redissolved with physiological solution and transferred to sterile vial using a sterile filter.

In a further aspect the present invention provides uses of folate radiopharmaceuticals of the invention for convenient and effective administration to a subject in need for diagnostic imaging.

Thus the present invention provides a method for diagnostic imaging of a cell or population of cells expressing a folate-receptor, said method comprising the steps of administering at least one folate radiopharmaceutical of the invention in a diagnostic imaging amount, and obtaining a diagnostic image of said cell or population of cells.

Such imaging may be performed on a cell or population of cells expressing a folate-receptor in vitro or in vivo.

Thus, the present invention provides a method for in vitro detection of a cell expressing the folate receptor in a tissue sample which includes contacting said tissue sample with at least one folate radiopharmaceutical of the invention in effective amounts and for sufficient time and conditions to allow binding to occur and detecting such binding by imaging techniques such as autoradiography and the like.

In a further aspect the present invention provides uses of folate radiopharmaceuticals of the present invention for convenient and effective administration to a subject in need for diagnostic imaging or monitoring of cancer or inflammatory and autoimmune disease therapy.

In another aspect the present invention provides a method for simultaneous diagnosis and therapy, comprising the steps of administering to a subject in need thereof at least one folate radiopharmaceutical of the present invention in a diagnostically effective amount in combination with a therapeutically active, and obtaining a diagnostic image of said tissues to follow the course of treatment.

The subject of the methods of the present invention is preferably a mammal, such as an animal or a human, preferably a human.

The dosage depends on the nature of the effect desired, such as the form of diagnosis or therapy, on the kind and frequency of treatment, on the diagnostic instrumentation, on the form of application of the preparation, and on the age, weight, nutrition and condition of the recipient, kind of concurrent treatment, if any.

However, the most preferred dosage can be tailored to the individual subject, as is understood and determinable by one of skill in the art, without undue experimentation. This typically involves adjustment of a standard dose, e.g., reduction of the dose if the patient has a low body weight.

Treatment can commence with a smaller amount, below the optimum amount, which can be increased in order to achieve the optimum effect.

The folate radiopharmaceuticals of the present invention may be administered either as a repeated dose or preferably as a single dose. For example, the folate radiopharmaceuticals of this invention may be administered to a subject by intravenous bolus injection. The suitable forms for injection include sterile aqueous solutions or dispersions of the above mentioned folate radiopharmaceuticals of the present invention.

For a solution to be injected a preferred unit dosage is from about 0.01 ml to about 10 ml. After e.g. intravenous administration, imaging of the organ or tumor in vivo can take place, if desired, from 30 min to 4 hours, after the radiolabeled reagent has been administered to a subject. Typically, a sufficient amount of the administered dose will accumulate in the targeted area.

The folate radiopharmaceuticals are preferably purified by HPLC. After removing the solvents of the HPLC purification the products were preferably solved in physiological solutions such as 0.9% NaCl or 0.15M phosphate buffer solution, before the application, the formulated radiopharmaceutical is transferred to a sterile vial via a sterile filter.

The folate radiopharmaceuticals of the invention may also be used for in vitro detection of a cell expressing the folate receptor in a tissue biopsy taken from a subject. Thus in a further embodiment the present invention provides a method for in vitro detection of a cell expressing the folate receptor, e.g. a tumor cell or an activated macrophage, in a tissue sample which includes contacting said tissue sample with a folate radiopharmaceutical of the present invention in effective amounts and for sufficient time and conditions to allow binding to occur and detecting such binding by imaging techniques.

Samples can be collected by procedures known to the skilled person, e.g., by collecting a tissue biopsy or a body fluid, by aspirating for tracheal or pulmonary samples and the like.

Tissue samples to be tested include any tissue suspected to contain a cell expressing a folate receptor, such as tumor cells, epithelial cells, kidneys, gastrointestinal or the hepatobiliary system, activated macrophages, monocytes, and others. Samples can be sectioned, e.g., with a microtome, to facilitate microscopic examination and observation. Samples can also be fixed with an appropriate fixative either before or after incubation with one of the folate radiopharmaceuticals of the present invention to improve the histological quality of sample tissues.

Time and conditions sufficient for binding of a folate radiopharmaceutical of the present invention to a folate receptor on the cell include standard tissue culture conditions, i.e. samples can be cultured in vitro and incubated with one of the compounds or compositions of the present invention in physiological media. Such conditions are well known to the skilled person. Alternatively, samples can be fixed and then incubated with a folate radiopharmaceutical of the present invention in an isotonic or physiological buffer.

For all applications it is convenient to prepare the compounds or compositions of the present invention at, or near, the site where they are to be used. All of the compounds and/or methods disclosed and claimed herein can be made and executed without undue experimentation in light of the present disclosure. It will be apparent to those of skill in the art that variations may be applied to the present invention without departing from the scope of the invention. The Examples provided herein are intended to be illustrative and are not exhaustive; therefore the illustrated Examples should not be viewed as limiting the invention in any way (see also Betzel et al. Bioconj. Chem. 2013, 24: 205-214).

EXAMPLES

General: Reagents and solvents were purchased from Sigma-Aldrich Chemie GmbH, Acros Organics or VWR International AG if nothing else is mentioned. All chemicals were used as supplied. Human and mouse (female CD-1) microsomes and the NADPH regenerating systems were purchased from BD biosciences.

Analytical Radio-HPLC: Analytic radio-high performance liquid chromatography (HPLC) was performed on an Agilent 1100 series HPLC system equipped with a GabiStar (Raytest) radiodetector using an RP-18 column, Luna PFP (2) C18, (5 μm, 250×4.6 mm, Phenomenex) with a solvent system and gradient as follows: eluent A was a $NaH_2PO_4$/$Na_2HPO_4$ buffer (0.05 M, pH 7.4) and eluent B was MeOH. A gradient from 0-30 min 100%-70% A was used at a flow rate of 1 ml/min. The specific activity was determined from a calibration curve obtained from different concentrations of the cold reference compound. To determine the amount of the chlorinated precursor (3'-aza-2'-chloro-folic acid), a standard curve obtained from different concentrations of 3'-aza-2'-chloro-folic acid was used.

Semipreparative Radio-HPLC: For purification, radio-HPLC was performed on a semipreparative HPLC system equipped with equipped with a Smartline Pump 1000, Smartline Manager 5000, Smartline UV detector 2500 (Knauer) and a GabiStar radiodetector (Raytest). [$^{18}$F]-3'-aza-2'-fluorofolic acid was purified on a RP-18 column, Luna PFP(2) C18, (5 μm, 250×10 mm, Phenomenex) with a solvent system as follows: eluent A was a solution of 0.1% EtOH in $NaH_2PO_4$/$Na_2HPO_4$ buffer (0.05 M, pH 7.4) and eluent B was a 40% solution of EtOH in $NaH_2PO_4$/$Na_2HPO_4$ buffer (0.05 M, pH 7.4). A gradient from 0-10 min 100%-85% A, 10-25 min isocratically 85% A was used at a flow rate of 4 ml/min.

Radio-UPLC: For stability studies, an ultra-performance liquid chromatography (UPLC™, Waters) system, equipped with an Acquity UPLC BEH C18 column (1.7 μm, 2.1×50 mm, Waters) and a coincidence detector (FlowStar LB513, Berthold) was used with following solvent system: eluent A was a $NaH_2PO_4$/$Na_2HPO_4$ buffer (0.05 M, pH 7.4) and eluent B was acetonitrile. A gradient from 0-4.0 min 100%-40% A, at a flow rate of 0.6 ml/min was used.

Production of No-Carrier-Added [$^{18}$F]Fluoride: No-carrier-added [$^{18}$F]fluoride was produced via the $^{18}$O(p,n)$^{18}$F nuclear reaction at a Cyclone 18/9 cyclotron (IBA). Isotopically 97% enriched $^{18}$O-water was irradiated by an 18 MeV proton beam using a 2.1-ml target. The target volume (1.95 ml) was transferred to a hot cell, using a helium stream. No-carrier-added [$^{18}$F]fluoride (40-80 GBq) was trapped on an anion exchange cartridge (Sep-Pak Light Accell Plus QMA, Waters), preconditioned with aqueous potassium carbonate solution (0.5 M, 5 ml) and water (10 ml).

Determination of the Log D: Determination of the log D value was performed, using the shake-flask-method, where the partition coefficient of the radiotracer between n-octanol and phosphate buffered saline (PBS) was determined (Wilson et al. 2001 Applied Radiation and Isotopes). n-Octanol (0.5 ml) and PBS (0.5 ml) were mixed in an Eppendorf tube containing the radioactive sample (5-10 μl). Tubes were shaken for 15 min at room temperature in an over-head shaker and afterwards centrifuged (3 min, 5000 rpm). From each Eppendorf tube, 50 μl of each phase were transferred into a vial for counting in a γ-counter. The log D value was calculated according to the following equation: $\log D_{7.4} = \log[\text{activity(octanol phase)/activity PBS phase)}]$.

Cell Culture: KB cells (human cervical carcinoma cell line, HeLa subclone; ACC-136) were purchased from the German Collection of Microorganisms and Cell Cultures (DSMZ, Braunschweig, Germany). The cells were cultured as monolayers at 37° C. in a humidified atmosphere containing 5% $CO_2$. Importantly, the cells were cultured in a folate-free cell culture medium, FFRPMI (modified RPMI, without folic acid, vitamin $B_{12}$ and phenol red; Cell Culture Technologies GmbH, Gravesano/Lugano, Switzerland). FFRPMI medium was supplemented with 10% heat-inactivated fetal calf serum (FCS, as the only source of folate), L-glutamine and antibiotics (penicillin/streptomycin/fungizone). Routine culture treatment was performed twice a week with EDTA (2.5 mmol/l) in PBS.

Example 1: Synthesis of precursor $N^2$-acetyl-3'-aza-2'-nitrofolic acid di-tert butyl ester (a) Synthesis of N-(6-amino-2-chloronicotinoyl)-L-glutamic acid di-tert butylester 6-amino-2-chloronicotinic acid (6 g, 34.8 mmol, purchased from Anichem Inc.) was dissolved in N,N-dimethylformamide (232 ml) at room temperature. The solution was cooled to 0° C. and triethylamine (11 ml, 7.39 g, 73.0 mmol) was added. After addition of HBTU (2-(1H-benzotriazol-1-yl)-1,1,3,3-tetramethyluronium hexa-fluorophosphate, 14.5 g, 38.2 mmol) the mixture was stirred for 5 min. at 0° C. and then di tert butyl-L-glutamate hydrochloride (10.8 g, 36.5 mmol) was added. The cooling bath was removed and the mixture was stirred for 18 hours. After cooling to −20° C. the solids were drawn off and washed with DMF (20 ml). The filtrate was evaporated to dryness under vacuum and the residue was dissolved in a mixture of ethylacetate (400 g) and methyl-tert butylether (200 g). The solution was washed three times with water (150 ml in total), three times with an aqueous 1 M $NaHCO_3$-solution (150 ml in total) and three times with an aqueous saturated NaCl-solution (150 ml in total). The organic layer was dried over magnesium sulfate (10 g) and evaporated to dryness under vacuum. The residue was purified by column chromatography on silica gel (n-hexane/ethyl acetate 7:3 to 5:5) to give N-(6-amino-2-chloronicotinoyl)-glutamic acid-di tert butylester as a pale yellow solid. Yield: 6.8 g (36.5 mmol, 47.3%).

HR-MS (ESI, sample dissolved in $CH_2Cl_2$): m/z $[MH]^+$ calcd. for $C_{19}H_{29}ClN_3O_5$: 414.1790; found: 414.1789.

$^1$H-NMR (200 MHz, DMSO-$d_6$):=1.39 (s, 9H, OtBu), 1.41 (s, 9H, OtBu), 1.71-2.07 (m, 2H, C($\beta$)$H_2$), 2.33 (t, 2H, C($\gamma$)$H_2$), 4.18-4.29 (m, 1H, $C_\alpha H$), 6.40 (d, 1H, 4'$H_{arom}$, $J^2$=8.3 Hz), 6.69 (s, 2H, $NH_2$), 7.47 (d, 1H, 5'$H_{arom}$, $J^2$=8.3 Hz), 8.36 (d, 1H, NH, $J^3$=7.6 Hz).

$^{13}$C-NMR (200 MHz, DMSO-$d_6$): 26.6, 28.2, 31.6, 52.9, 80.2, 81.1, 106.3, 118.9, 140.1, 146.2, 160.6, 166.2, 171.2, 172.0.

(b) Synthesis of $N^2$-acetyl-3'-aza-2'-chlorofolic acid di-tert butyl ester

N-(6-amino-2-chloronicotinoyl)-glutamic acid-di tert butylester (0.5 g, 1.27 mmol) and $N^2$-acetyl-6-formylpterin (0.3 g, 1.21 mmol) was dissolved in acetic acid (30 ml). After addition of tetraethyl orthosilicate (0.54 ml, 1.27 mmol) the mixture was stirred at 55° C. for 6 hours. After cooling to room temperature over night, sodium triacetoxyborohydride (0.27 g, 2.42 mmol) was added and the mixture was stirred for 1 hour at room temperature. After addition of n-hexane (18 g) and water (8 g) the organic layer was separated and the aqueous layer was evaporated to dryness under vacuum. The residue was suspended in a mixture of water (9 g) and acetonitrile (1 g). The solids were drawn off and washed two times with water (10 g in total) to give crude $N^2$-acetyl-3'-aza-2'-chlorofolic acid di tert butylester (0.77 g). The crude product was purified by repeated digestion in mixtures of water and acetonitrile with an increasing percentage of acetonitrile from 10% to 25% to give $N^2$-acetyl-3'-aza-2'-chlorofolic acid di tert butylester as an orange solid. Yield: 0.61 g (0.911 mmol, 75%).

HR-MS (ESI, sample dissolved in $MeOH/CH_2Cl_2/1:1$): m/z $[MH]^+$ calcd. for $C_{28}H_{35}ClN_8NaO_7$: 653.2209; found: 653.2211.

$^1$H-NMR (200 MHz, DMSO-$d_6$):=1.37 (s, 9H, OtBu), 1.39 (s, 9H, OtBu), 1.75-1.82 (m, 1H, C($\beta$)H), 1.92-1.99 (m, 1H, C($\beta$)H'), 2.20 (s, 3H, $CH_3$), 2.28-2.32 (m, 2H, C($\gamma$)$H_2$), 4.21 (m, 1H, C($\alpha$)H), 4.72 (d, 2H, C(6)$CH_2$, J=5.8 Hz), 6.71 (s, 1H, 4'Harom), 8.00 (bt, 1H, NH), 8.04 (s, 1H, 5'$H_{arom}$), 8.50 (d, 1H, NH(Glu), J=7.5 Hz), 8.83 (s, 1H, C(7)H), 11.9 (bs, 1H, NH), 12.3 (bs, 1H, NH).

$^{13}$C-NMR (200 MHz, DMSO-$d_6$): 24.4, 26.5, 28.1, 28.2, 31.5, 44.5, 52.8, 80.3, 81.1, 107.1, 119.6, 130.9, 139.7, 145.9, 149.7, 150.2, 152.4, 154.9, 158.6, 159.7, 166.1, 171.1, 171.9, 174.6.

(c) Synthesis of N-(6-amino-2-nitronicotinoyl)-L-glutamic acid di tert-butylester The synthesis was achieved following the procedure described in Example 1a) but using 6-amino-2-nitronicotinic acid instead of 6-amino-2-chloro-nicotinic acid.

(d) Synthesis of $N^2$-acetyl-3'-aza-2'-nitrofolic acid di-tert butyl ester

The synthesis was achieved following the procedure described in Example 1b) but using N-(6-amino-2-nitronicotinoyl)-L-glutamic acid di tert-butylester instead of N-(6-amino-2-chloronicotinoyl)-glutamic acid-di tert butylester.

Example 2: Synthesis of No-Carrier-Added 3'-aza-2'-[$^{18}$F]fluorofolic acid

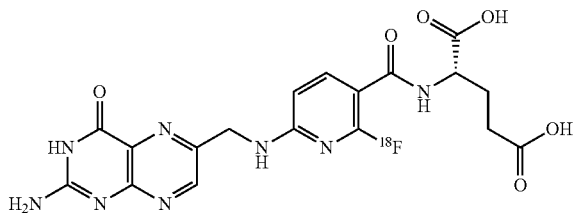 [SMILES: Nc1nc2ncc(CNc3ccc(C(=O)N[C@@H](CCC(=O)O)C(=O)O)c([18F])n3)nc2c(=O)[nH]1]

The no-carrier-added [$^{18}$F]fluoride trapped on the anion exchange cartridge was directly eluted into a 5 ml sealed reaction vessel, using a solution of caesium carbonate (2.8 mg) and Kryptofix 2.2.2 (5 mg) in a mixture of acetonitrile (1.4 ml) and water (0.6 ml). The solvent was removed at 90° C. under vacuum and a stream of nitrogen. Subsequently, dry acetonitrile (3×1 ml) was added and evaporated to dryness. Then, only vacuum was applied for 10 min at 90° C.

The precursor, $N^2$-acetyl-3'-aza-2'-chlorofolic acid di-tertbutyl ester (2.50 mg, 3.96 µmol) or alternatively $N^2$-acetyl-3'-aza-2'-nitro-folic acid di-tert butyl ester, was added to the dry [$^{18}$F]fluoride-cryptate complex in dimethyl sulfoxide (300 µl). The mixture was heated to 160° C. for 10 min. After 10 min of cooling and addition of water (5 ml), the mixture was passed through a reversed-phase cartridge (Sep-Pak C18 Plus; Waters), which was preconditioned with methanol (5 ml) and rinsed with water (10 ml). The loaded cartridge was washed with water (3×8 ml). The $^{18}$F-labeled protected intermediate, $N^2$-acetyl-3'-aza 2'-fluorofolic acid di-tertbutyl ester, was eluted with acetonitrile (2 ml) into another 5 ml sealed reaction vessel. The volume of acetonitrile was concentrated to approx. 0.1 ml under reduced pressure and a nitrogen stream at 90° C. For hydrolysis, a hydrogen chloride solution (4 M, 1.25 ml) was added and the mixture was heated for 10 min at 60° C. After 5 min of cooling, the mixture was neutralized by addition of a sodium hydroxide solution (5 M, 1.0 ml) and diluted with $NaH_2PO_4$/$Na_2HPO_4$ buffer (0.05 M, pH 7.4, 2.5 ml) to a total volume of 5 ml. The solution was injected into the semipreparative radio-HPLC system. The collected product fraction ($t_R$=21 min), containing 6% EtOH, was passed through a sterile filter into a sterile, pyrogen-free vial, ready to use for further experiments (in vitro and in vivo).

Figure 2:
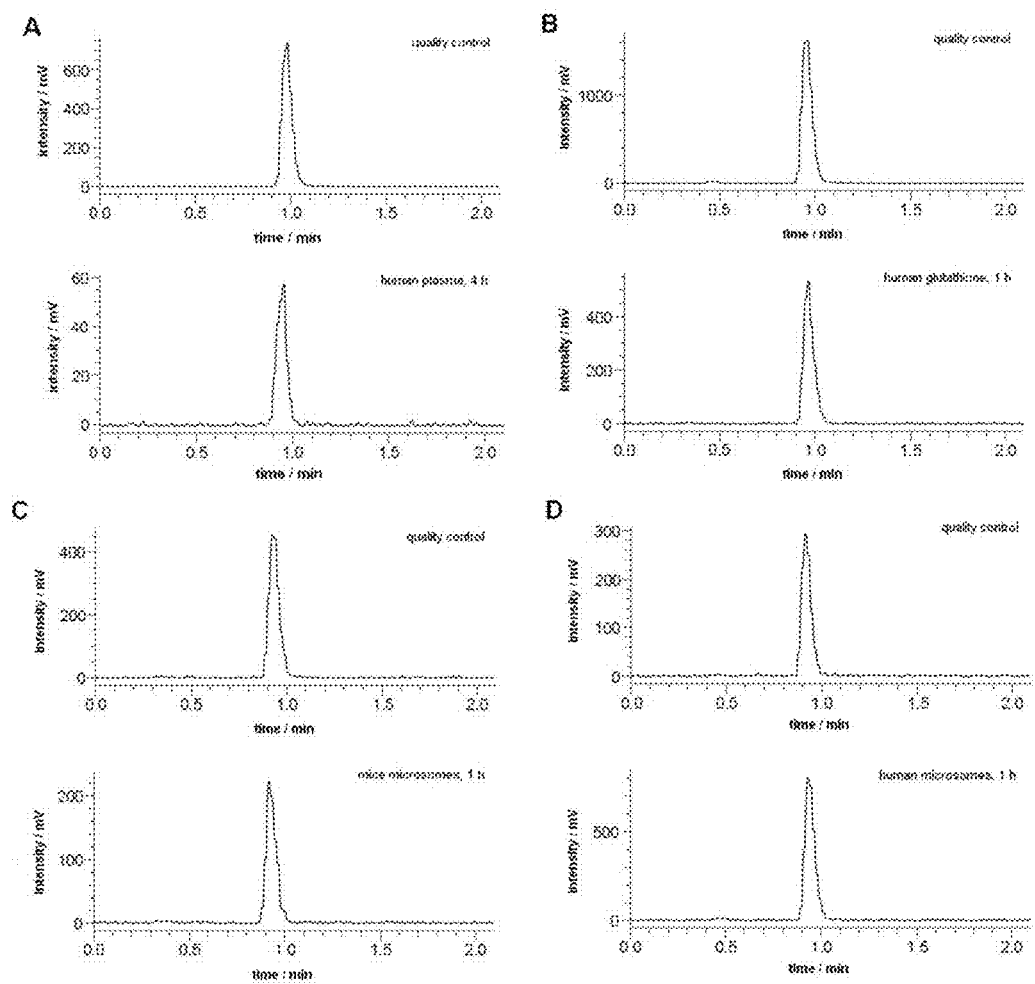
FIG. 2. Stability of 3'-aza-2'-[$^{18}$F]fluorofolic acid in A: human blood plasma, 4 h; B: human glutathione, 1 h; C: mouse microsomes, 1 h; D: human microsomes, 1 h.
Figure 3:
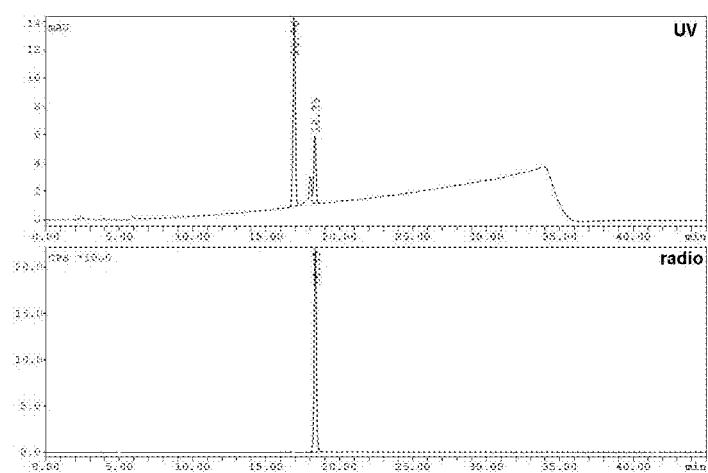
FIG. 3. Quality control of the 3'-aza-2'-[$^{18}$F]fluorofolic acid after HPLC purification.

The decay-corrected radiochemical yield ranged from 5-15% (0.5-2.75 GBq). Quality control was performed on an analytical radio-HPLC (FIG. 2). Radiochemical purity was greater than 98% and the specific activity ranged from 45-126.8 GBq/µmol. The amount of chlorinated byproduct was less than 17 µg/mL of the formulated product solution (1-16.3 µmol/ml range). The total synthesis time was about 85 min and the identity of [$^{18}$F]-3'-aza-2'-fluorofolic acid was confirmed by coinjection with the reference compound 3'-aza-2'-[$^{19}$F]fluorofolic acid. A summary of the radiolabeling conditions is shown in Table 1.

TABLE 1

Conditions for the synthesis of 3'-aza-2'-[$^{18}$F]fluorofolic acid:

| Step 1- Radiolabeling | |
|---|---|
| Precursor | 4.0 µmol (2.5 mg) |
| Solvent | 300 µl DMSO |
| Temperature | 160° C. |
| Reaction time | 10 min |
| Step 2 - Purification of the $^{18}$F-Labeled Aza-Folate | |
| tC18 plus cartridge | Removal of unreacted [$^{18}$F]fluoride and salts |
| Step 3 - Deprotection of the $^{18}$F-Labeled Aza-Folate | |
| 4N HCl | 1.25 ml |
| Temperature | 60° C. |
| Reaction time | 10 min |
| 5N NaOH (neutralization) | 1.0 ml |
| Step 4 - Purification of the Final Radiotracer (5) | |
| Radiochemical purity | >98% |
| Radiochemical yield (decay corrected) | 5-15% |
| Radioactivity | Max. 2.75 GBq |

Log $D_{7.4}$ measurement: For the assessment lipophilicity, the partition coefficient of [$^{18}$F]-3'-aza-2'-fluoro-folic acid in n-octanol/PBS was found to be −4.2±0.1 (n=10), indicating very hydrophilic properties of [$^{18}$F]-3'-aza-2'-fluoro-folic acid.

Example 3: Modular GMP-Radiosynthesis of 3'-aza-2'-[$^{18}$F]fluoro-folic acid The GMP production of the radiotracer 3'-aza-2'-[$^{18}$F] fluoro-folic acid was performed on an automated synthesis module. No-carrier-added [$^{18}$F]fluoride was trapped on an anion exchange cartridge and directly eluted into the reactor by the use of a mixture of caesium carbonate (2.8 mg in 0.35 ml H$_2$O) and Kryptofix 2.2.2 (6.5 mg in 0.35 ml acetonitrile). The solvent was removed at 120° C. under reduced pressure and a stream of nitrogen. Acetonitrile (0.1 ml) was added and evaporated to dryness.

The precursor solution of N$^2$-acetyl-3'-aza-2'-chlorofolic acid di-tertbutyl ester (2.50 mg, 3.96 µmol) in DMSO (400 µL) was added to the dry [$^{18}$F]fluoride-cryptate complex. The mixture was heated to 150° C. for 17 min. Then, 4 M HCl (1.0 ml) was directly added into the reactor and hydrolysis was achieved at 60° C. for 10 min. The reaction mixture was diluted with H$_2$O (9 ml) and loaded on an activated MCX cartridge and washed with H$_2$O (5 ml). By rinsing the cartridge with a solution made of 10% MeOH in 50 mM phosphatebuffer pH 7.4 (4 ml) the radiotracer was eluted. The eluent was injected into a semipreparative radio-HPLC system. The collected product fraction (t$_R$=21.1 min) was acidified with 4 M HCl (0.5 ml) and loaded onto another MCX cartridge. After rinsing the cartridge with H$_2$O (5 ml), the radiotracer was eluted with 10% EtOH in 50 mM phosphate buffer pH 7.4 (5 mL) and diluted with 0.9% aq. NaCl (9 mL).

The decay-corrected radiochemical yield at end of synthesis ranged from 7-16% (2.4-6.0 GBq). Quality control was performed on an analytical radio-HPLC. Radiochemical purity was greater than 99% and the specific activity ranged from 47-62 GBq/µmol. The amount of chlorinated byproduct was less than 0.1 µg/ml of the formulated product solution. The total synthesis time was about 75 min. A summary of the radiolabeling conditions is shown in Table 2.

TABLE 2

Conditions for the synthesis of 3'-aza-2'-[$^{18}$F]fluoro-folic acid on an automated module.

| Step 1- Radiolabeling | |
|---|---|
| Precursor | 4.0 µmol (2.5 mg) |
| Solvent | 400 µl DMSO |
| Temperature | 150° C. |
| Reaction time | 17 min |
| Step 2 - Deprotection of the $^{18}$F-Labeled Aza-Folate | |
| 4M HCl | 1.0 ml |
| Temperature | 60° C. |
| Reaction time | 10 min |
| H$_2$O (dilution) | 9.0 ml |
| Step 3 - Purification of the Final Radiotracer | |
| MCX cartridge (60 mg) | Trapping of radiotracer and removal of unreacted [$^{18}$F]fluoride and salts |
| Elution | 4 mL 10% MeOH in 50 mM phosphate buffer pH 7.4 |
| HPLC | Luna PFP(2), 250 × 10 mm, 7% MeOH in 20 mM phosphate buffer pH 7.4 |
| MCX cartridge (30 mg) | Trapping of HPLC product fraction, removal of HPLC solvent |
| Step 4 - Formulation | |
| Elution | 10% EtOH in 50 mM phosphate buffer pH 7.4 (5 ml) and 0.9% NaCl (9 mL) |
| Radiochemical purity | >99% |
| Radiochemical yield (decay corrected) | 7-16% |
| Radioactivity | max. 6.0 GBq |

Example 4: Synthesis of No-Carrier-Added [$^{18}$F]-3', 5'-diaza-2'-fluorofolic acid The synthesis was performed in analogy to Examples 1 to 3 but using 2-amino-4-chloro-5-pyrimidinecarboxylic acid (purchased from Abby Pharmatech, LLC) instead of 6-amino-2-chloronicotinic acid.

Example 5: Synthesis of [$^{19}$F]-Reference Compounds (a) Synthesis of N-(6-amino-2-fluoronicotinoyl)-L-glutamic acid-di tert butylester

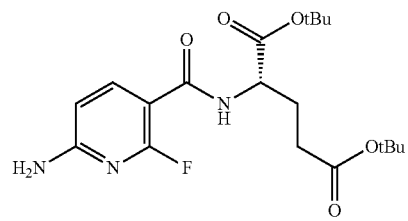 [SMILES: CC(C)(C)OC(=O)CC[C@H](NC(=O)c1ccc(N)nc1F)C(=O)OC(C)(C)C]

To a solution of 6-amino-2-fluoronicotinic acid hydrochloride (5.72 g, 29.7 mmol, purchased from Anichem Inc.) in N,N-dimethylformamide (50 ml) was added N-hydroxysuccinimide (6.83 g, 59.3 mmol). After cooling to 0° C. triethylamine (15.01 g, 148.3 mmol) was added dropwise within 10 minutes. The mixture was warmed up to room temperature and N,N-diisopropylcarbodiimide (6.9 ml, 44.5 mmol) was added within 5 minutes. After 29 hours a solution of glutamic acid di tert butylester hydrochloride (17.6 g, 59.3 mmol) in N,N-dimethylformamide (114 ml)

was added dropwise within 5 minutes. After 21 hours solids were drawn off and washed two times with N,N-dimethylformamide (in total 40 ml). The filtrate and the washings were combined and diluted with ethylacetate (500 ml) and diisopropylether (500 ml). The solution was washed five times with water (in total 1000 ml). The organic layer was dried over magnesium sulfate (60 g) and over aluminum oxide (10 g) and evaporated to dryness in vacuum. Acetonitrile (57.9 g) was added to the residue and solids were drawn off and washed with acetonitrile (in total 20 g). The washings and the filtrate were combined and evaporated to dryness under vacuum at 40° C. The residue was purified by column chromatography on silica gel (n-hexane/ethyl acetate 7:3 to 0:1, Rf=0.46, n-hexane/ethyl acetate 7:3) to give N-(6-amino-2-fluoronicotinoyl)-L-glutamic acid-di tert butylester as a crystalline solid after evaporation of product fractions. Yield: 2.27 g (5.7 mmol, 19%).

HR-MS (ESI, sample dissolved in water/CH$_3$CN/1:1): m/z [MH]$^+$ calcd. for C$_{19}$H$_{29}$FN$_3$O$_5$: 398.2086; found: 398.2083.

$^1$H-NMR (200 MHz, DMSO-d$_6$): δ=1.37 (s, 9H, OtBu), 1.41 (s, 9H, OtBu), 1.79-1.98 (m, 2H, C(β)H$_2$), 2.29 (t, 2H, C(γ)H$_2$), 4.33 (m, 1H, C(α)H), 6.36 (dd, 1H, 4'Harom, $^3J_{HH}$=8.4 Hz, $^5J_{FH}$=2.2 Hz), 6.91 (bs, 2H, NH$_2$), 7.78-7.87 (m, 2H, NH, 5'H$_{arom}$).

$^{13}$C-NMR (400 MHz, DMSO-d$_6$): 26.1, 27.6, 27.7, 31.1, 52.3, 79.7, 80.7, 101.6 (d, $^2J_{CF}$=27.4 Hz), 104.7 (d, $^4J_{CF}$=2.8 Hz), 142.1 (d, $^3J_{CF}$=3.0 Hz), 160.0 (d, $^1J_{CF}$=237.0 Hz), 160.7 (d, $^3J_{CF}$=19.3 Hz), 162.9 (d, $^3J_{CF}$326.5 Hz), 170.8, 171.5.

(b) Synthesis of N$^2$-Acetyl-3'-aza-2'-fluorofolic acid di tert butylester

N$^2$-Acetyl-6-formylpterin (1.17 g, 5.03 mmol) was suspended in acetic acid (25 ml) at room temperature. A solution of N-(6-amino-2-fluoronicotinoyl)-L-glutamic acid-di tert butylester (1.00 g, 2.52 mmol) in acetic acid (35 ml) was added dropwise to the suspension within 30 min. After 2 hours at room temperature a clear solution has formed and molecular sieve 4A (10 g) was added. After further 2.5 hours a second portion of molecular sieve 4A (10 g) was added. After 2 hours sodium triacetoxyborohydride (0.5 g, 2.39 mmol) was added and after one further hour a second portion of sodium triacetoxyborohydride (0.5 g, 2.39 mmol) was added. After 16 hours at room temperature a third portion of sodium triacetoxyborohydride (0.53 g, 2.52 mmol) was added. After further 2.5 hours solids were drawn off from the reaction mixture and washed with acetic acid (30 ml). The filtrate was added dropwise to a mixture of water (150 ml) and acetonitrile (30 ml). Then water (100 ml) was added dropwise. The mixture was cooled to 4° C. for two hours and the precipitated product was drawn off. The product was suspended four times in water (40 g in total) and then dried in vacuum over P$_2$O$_5$ to give N$^2$-acetyl-3'-aza-2'-fluorofolic acid di tert butylester as an off-white powder. Yield: 1.10 g (1.79 mmol, 71%).

HR-MS (ESI, sample dissolved in water/CH$_3$CN/1:1): m/z [MH]$^+$ calcd. for C$_{28}$H$_{36}$FN$_8$O$_7$: 615.2685; found: 615.2677.

$^1$H-NMR (200 MHz, DMSO-d$_6$): δ=1.37 (s, 9H, OtBu), 1.40 (s, 9H, OtBu), 1.80-2.07 (m, 2H, C(β)H$_2$), 2.21-2.32 (t, 2H, C(γ)H$_2$), 4.29 (m, 1H, C(α)H), 4.71 (d, 2H, C(6)CH$_2$); 6.56 (dd, 1H, 4'Harom, $^3J_{HH}$=8.4 Hz, $^5J_{FH}$=2.2 Hz), 7.83 (dd, 1H, 4'Harom, $^3J_{HH}$=8.4 Hz, $^4J_{FH}$=10.0 Hz), 7.91 (dd, 1H, NH(Glu), $^3J_{HH}$=7.4 Hz, $^4J_{HH}$=4.5 Hz), 8.29 (t, 1H, $^3J_{HH}$=5.7 Hz), 8.88 (s, 1H, C(7)H), 11.94 (bs, 1H, N(3)H), 12.28 (bs, 1H, NHAc).

$^{13}$C-NMR (400 MHz, DMSO-d$_6$): 23.9, 26.1, 27.7, 27.6, 31.1, 44.1, 52.3, 79.7, 80.7, 102.5 (d, $^2J_{CF}$=28.3 Hz), 105.4, 130.5, 141.7, 149.3, 149.4, 151.7, 154.5, 158.9 (d, $^3J_{CF}$=17.8 Hz), 159.3, 159.8 (d, $^1J_{CF}$=237.6 Hz), 162.9 (d, $^3J_{CF}$=6.5 Hz), 170.7, 171.5, 174.1.

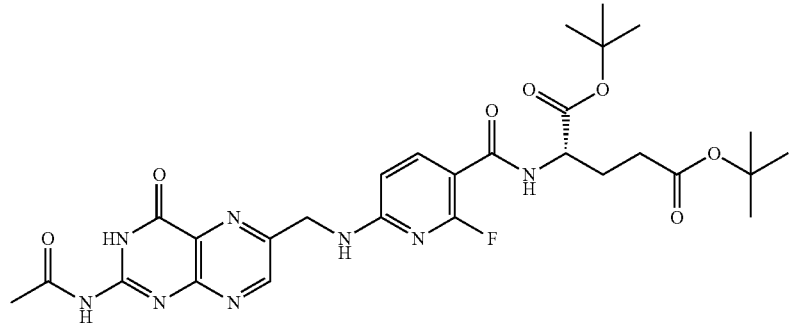 [SMILES: CC(=O)Nc1nc2ncc(CNc3ccc(C(=O)N[C@@H](CCC(=O)OC(C)(C)C)C(=O)OC(C)(C)C)c(F)n3)nc2c(=O)[nH]1]

(c) Synthesis of 3'-aza-2'-fluorofolic acid

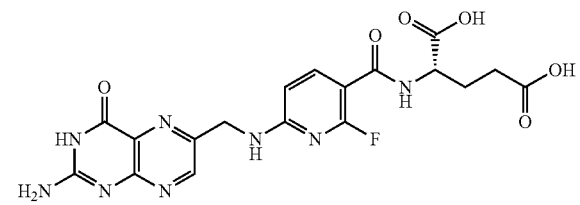 [SMILES: Nc1nc2ncc(CNc3ccc(C(=O)N[C@@H](CCC(=O)O)C(=O)O)c(F)n3)nc2c(=O)[nH]1]

N$^2$-Acetyl-3'-aza-2'-fluorofolic acid di tert butylester (0.6 g, 1 mmol) was suspended in a mixture of 1M aqueous hydrochloric acid (16 ml) and acetonitrile (1.6 ml). The suspension was heated to 60° C. for 2 hours. After cooling to 4° C., the precipitated product was drawn off, washed with water (10 ml in total) and dried in vacuum over $P_2O_5$ to give crude 3'-aza-2'-fluorofolic acid as a light-yellow powder. Yield: 0.4 g (0.9 mmol, 88%). Crude 3'-aza-2'-fluorofolic acid (0.27 g, 0.59 mmol) was dissolved in a mixture of water (2 ml) and an 1M aqueous solution of sodium hydroxide (1.2 ml). The solution was treated with charcoal (0.027 g) for 15 minutes at 70° C. The charcoal was drawn off and the filtrate was cooled to 0° C. The product was precipitated by addition of aqueous 2M hydrochloric acid (0.59 ml). The precipitate was isolated by centrifugation. The mother liquor was decanted from the solid and the solid was washed three times with water (total amount: 14.2 ml). The solid residue was dried in vacuum at 20° C. to give 3'-aza-2'-fluorofolic acid as a yellow powder. Yield: 78 mg, (0.17 mmol, 29%).

HR-MS (ESI, sample dissolved in $CH_2Cl_2$ using 3-hydroxypicolinic acid as matrix): m/z $[MH]^+$ calcd. for $C_{18}H_{18}FN_8O_6$: 461.1328; found: 461.1328.

$^1$H-NMR (500 MHz, $D_2O$): δ=1.88-1.96 (m, 1H, C(β)H), 2.03-2.10 (m, 1H, C(β)H'), 2.14-2.24 (m, 2H, C(γ)$H_2$), 4.24-4.26 (m, 1H, C(α)H), 4.57 (s, 2H, C(6)$CH_2$), 6.47 (dd, 1H, 5'Harom, $^3J_{HH}$=8.6 Hz, $^5J_{FH}$=1.8 Hz), 7.85 (dd, 1H, 4'Harom, $^3J_{HH}$=10.1 Hz, $^4J_{FH}$=8.6 Hz), 8.5 (s, 1H, C(7)H).

$^{13}$C-NMR (500 MHz, $D_2O$): 23.4, 28.7, 34.1, 44.3, 55.8, 101.7, 101.9, 105.9, 128.2, 142.2, 146.6, 147.4, 155.7, 159.4, 159.8, 164.2, 165.2, 165.3, 173.2, 178.8, 181.5, 182.3.

(d) Synthesis of N-(2-amino-4-fluoropyrimidine-5-carbonyl)-L-glutamic acid-di tert butylester The synthesis was achieved following the procedure described in example 5a) but using 2-amino-4-fluoro-5-pyrimidinecarboxylic acid (purchased from Abby Pharmatech, LLC) instead of 6-amino-2-fluoronicotinic acid.

(e) Synthesis of $N^2$-Acetyl-3',5'-diaza-2'-fluorofolic acid di tert butylester The synthesis was achieved following the procedure described in example 5b) but using N-(2-amino-4-fluoropyrimidine-5-carbonyl)-L-glutamic acid di-tert butylester instead of N-(6-amino-2-fluoronicotinoyl)-L-glutamic acid-di tert butylester.

(f) Synthesis of 3',5'-diaza-2'-fluorofolic acid

The synthesis was achieved following the procedure described in example 5c) but using $N^2$-Acetyl-3',5'-diaza-2'-fluorofolic acid di tert butylester instead of $N^2$-Acetyl-3'-aza-2'-fluorofolic acid di tert butylester.

Example 6: Partition Coefficient

For log $D_{7.4}$ determination a phosphate buffer was prepared, making a solution of $KH_2PO_4$ (1.743 g, 12.81 mmol) and $Na_2HPO_4 \cdot 2H_2O$ (9.596 g, 53.91 mmol) in water (1000 ml). A saturated solution of phosphate buffer in n-octanol and a saturated solution of n-octanol in phosphate buffer were prepared. The PBS solution (500 μl) and n-octanol solution (500 μl) were pipetted into an Eppendorf tube and the radiotracer (5-10 μl) was added. The Eppendorf tube was shaken for 15 min at room temperature in an over-head shaker. The two phases were separated by centrifugation at 5000 rpm for 3 min. An aliquot of each phase (50 μl) was transferred into an empty Eppendorf tube for counting in a γ-counter (Wizard, PerkinElmer). By calculating the logarithm of the ratio of the counts in the n-octanol and the PBS phase, the log $D_{7.4}$ value was determined. Values represent the mean of 10 determinations from two independent experiments. The log $D_{7.4}$ determination reveals the hydrophilic properties of [$^{18}$F]-2'-fluoro-3'-aza-folic acid, resulting in a value of −4.2±0.1.

Example 7: Stability Experiments (a) Human Plasma Stability

The radiotracer was tested with regard to its stability in human blood plasma over a period of 4 hours at 37° C. The formulated product (200 μL) was diluted with sodium phosphate buffer (100 μl) and an aliquot (60 μl, 15 MBq) was added to human plasma (500 μL), pre-incubated at 37° C. The mixture was shaken on a Thermomixer compact (Eppendorf) at 37° C. and 500 rpm. After several time points (0, 30, 60, 120, 150 and 240 min) aliquots were taken after tracer addition. Each aliquot (70 μl) was added to ice-cold MeOH (150 μl) to precipitate the proteins. To separate the supernatant from the precipitate, the suspension was centrifuged for 10 min at 13400 rpm (Eppendorf MiniSpin) at room temperature. The supernatant was passed through a microfilter (Sartorius Stedim Biotech GmbH, Minisart RC 25, 0.45 μm) and was analyzed on the radio-UPLC system.

(b) Stability Experiments Using Liver Microsomes

To a mixture of $KH_2PO_4/K_2HPO_4$ buffer (pH 7.4, 0.5 M, 200 μl), NADPH regenerating system A (50 μl), NADPH regenerating system B (10 μl), an aliquot of [$^{18}$F]-3'-aza-2'-fluorofolic acid (38 μl, approx. 15 MBq) was added and filled up with water (677 μl) to a volume of 975 μl and preincubated at 37° C. Then, mouse or human liver microsomes (20 mg/ml, 25 μl) were added and incubated at 37° C. After several time points (0, 20, 40 and 60 min) aliquots (100 μl) were drawn and the enzymatical reaction was stopped by purring the solution into ice-cold methanol (200 μl). Each sample was diluted with $NaH_2PO_4/Na_2HPO_4$ buffer (pH 7.4, 0.05 M, 600 μl). Every time point was performed as a triplicate and analyzed on a radio-UPLC system. As a negative control, samples were incubated without microsomes or without the NADPH regenerating system.

As a positive control experiment, testosterone instead of the radioactive tracer was incubated with the reaction mixture.

(c) Stability Experiments Using Liver Glutathione

Glutathione (0.1 M, 100 μl), S9-fraction (20 mg/ml, 50 μl) and $KH_2PO_4/K_2HPO_4$ buffer (pH 7.4, 0.5 M, 200 μl) were diluted with water (612 μl) to a volume of 772 μl and [$^{18}$F]-3'-aza-2'-fluorofolic acid (38 μl, approx. 15 MBq) was added. The mixture was incubated at 37° C. At several time points aliquots (100 μl) were drawn and the reaction was stopped by pouring the sample into ice-cold methanol (200 μl). Each sample was diluted with $NaH_2PO_4/Na_2HPO_4$ buffer (pH 7.4, 0.05 M, 600 μl). Every time point was performed as duplicates and analyzed on a radio-UPLC system.

In summary, HPLC analysis at all time points of investigation (over a time period of 1 h) resulted in the detection of only intact product, which indicates that radio-defluorination or metabolic processes did not occur, and 3'-aza-2'-[$^{18}$F]fluorofolic acid was completely stable over the whole period of investigation (FIG. 2).

Example 8: In Vitro Internalization Studies

Figure 5:
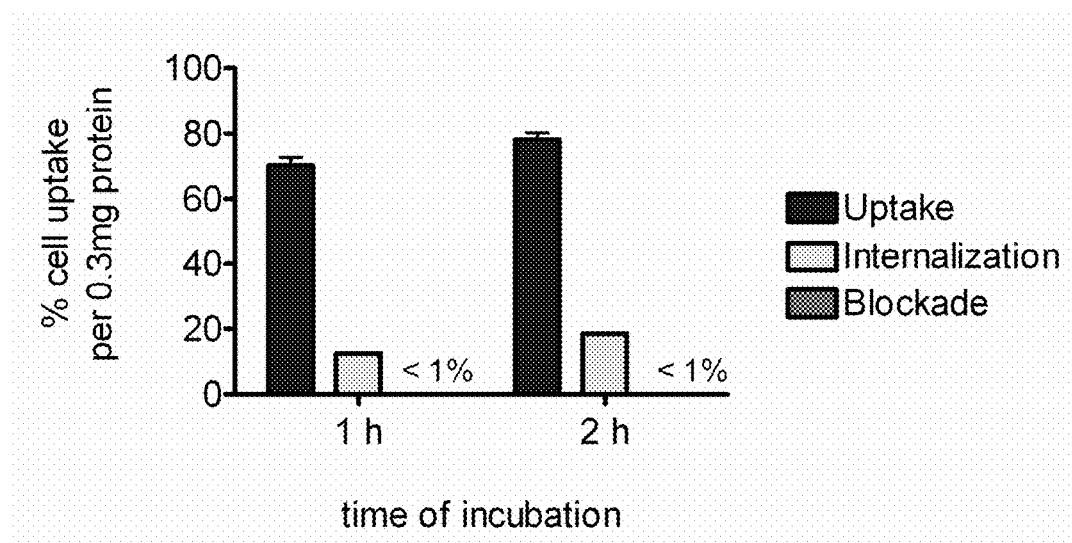
FIG. 5. Results of cell uptake studies of 3'-aza-2'-[$^{18}$F] fluorofolic acid: total uptake (blue), internalized fraction (yellow) and uptake under blockade conditions (red/not visible).

KB cells were seeded in 12-well plates to grow over night (~700,000 cells in 2 ml FFRPMI medium/well). [$^{18}$F]-3'- aza-2'-fluorofolic acid (25 L, 170 kBq) was added to each well. In some cases cells were incubated with excess folic acid (100 M) to block FRs on the surface of KB cells. After incubation for 1 h or 2 h at 37° C. the cells were washed three times with PBS to determine total cell uptake of 3'-aza-2'-[$^{18}$F]fluorofolic acid. In order to assess the fraction of 3'-aza-2'-[$^{18}$F]fluorofolic acid that was internalized, KB cells were washed with a stripping buffer (aqueous solution of 0.1 M acetic acid and 0.15 M NaCl, pH 3) to release FR-bound radiotracer from the cell surface. Cell lysis was accomplished by addition of 1 ml NaOH 1N to each well. The cell suspensions were transferred to 4 ml tubes and the samples were counted in a –counter. After homogenization by vortex, the concentration of proteins was determined for each sample by a Micro BCA Protein Assay kit in order to standardize measured radioactivity to the average content of 0.3 mg protein in a single well. Cell uptake studies of the radioproduct showed a specific uptake and internalization as it was blockable with excess folic acid. After two hours of incubation, the uptake was about 78.17% of total cell uptake and the internalized fraction accounted for 18.56%. Co-incubation of excess folic acid resulted in an inhibition of radiotracer uptake of 0.03 (FIG. 5).

Example 9: Ex Vivo Metabolite Studies

For the determination of radiometabolites in vivo, 3'-aza-2'-[$^{18}$F]fluorofolic acid (60-70 MBq) was intravenously injected into KB tumor bearing mice (n=2). After 5 min, blood samples were drawn from the opposite vein and the animals were sacrificed 30 min after radiotracer injection. The whole blood, liver, tumor and urine were collected. Blood samples were centrifuged at 5000 g for 5 min at 4° C. The proteins of the plasma samples were precipitated by addition of the same volume of ice-cold methanol followed by centrifugation. The supernatants of the plasma and the urine sample were diluted with PBS buffer and analyzed by radio-UPLC. Liver and tumor tissue were homogenized in an equal volume of PBS using a PT 1200 C Polytron (Kinematica AG), respectively. After addition of the same volume of ice-cold MeOH, the mixture was centrifuged at 5000 g for 5 min and 4° C. The supernatant was cleared from remaining proteins by addition of ice-cold methanol, followed by centrifugation. The resulting supernatant fractions were diluted with PBS buffer and analyzed by radio-UPLC.

Figure 4:
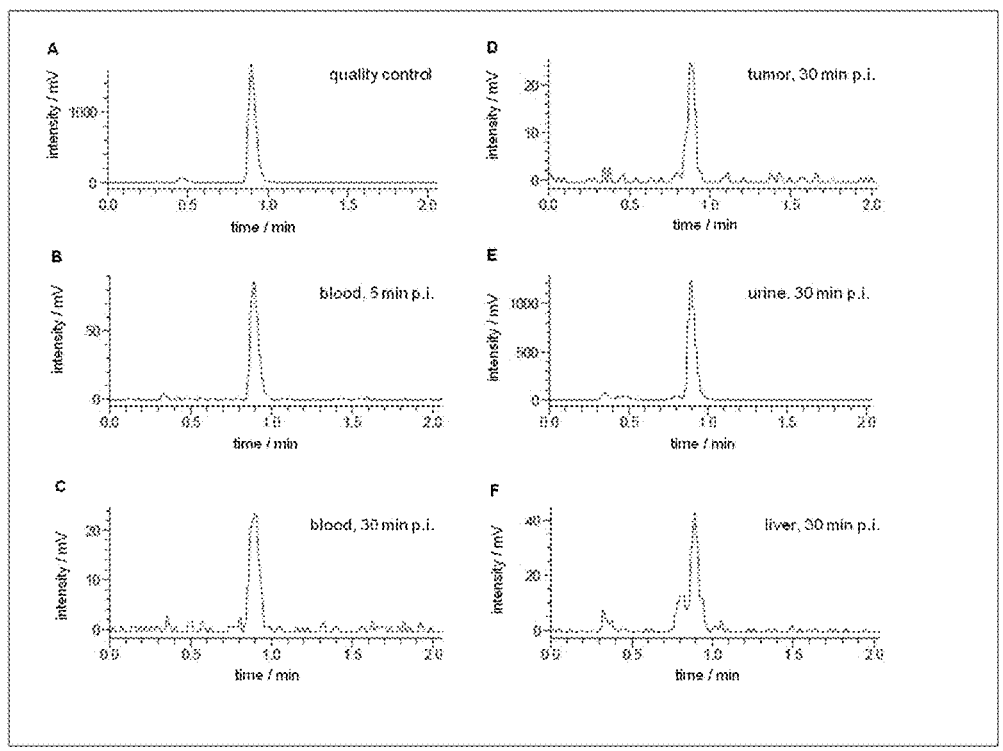
FIG. 4. Metabolite studies of 3'-aza-2'-[$^{18}$F]fluorofolic acid, radio-UPLC chromatograms of A: quality control, B: blood sample 5 min p.i., C: blood sample 30 min p.i., D: tumor 30 min p.i., E: urine 30 min p.i., F: liver 30 min p.i.

Analysis of the plasma samples (5 min and 30 min) as well as samples of urine and tumor revealed no detectable amounts of metabolites. In contrast, analysis of the liver sample showed signs of metabolism (FIG. 4).

Example 10: Folate Receptor Binding Affinity

Binding assays with the nonradioactive reference compound 3'-aza-2'-fluorofolic acid were performed with KB tumor cells suspended in PBS pH 7.4 (7'000 cells/240 L per Eppendorf tube). The cells were incubated in triplicate with $^3$H-folic acid (10 L, 0.84 nM) and increasing concentrations of 3'-aza-2'-fluorofolic acid ($5.0 \times 10^{-7}$ to $5.0 \times 10^{-12}$ M in 250 L PBS pH 7.4) on a shaker at 4° C. for 30 min. Nonspecific binding was determined in the presence of excess folic acid ($10^{-4}$ M). After incubation, Eppendorf tubes containing the cell suspensions were centrifuged at 4° C. for 5 min and the supernatant was removed. By addition of 0.5 ml of NaOH 1 M the cell pellets were lysed and transferred into scintillation tubes containing 5 ml of scintillation cocktail (Ultima Gold; Perkin Elmer). Radioactivity was measured using a liquid scintillation analyzer (Tri-Carb 1900 TR, Packard) and an inhibitory concentration of 50% was determined from displacement curves using GraphPad Prism (version 5.01) software.

Determination of FR-binding affinity of the non-radioactive reference compound 3'-aza-2'-fluorofolic acid resulted in an $IC_{50}$ value of $0.81 \pm 0.18$ nM. This value is in the same range as the $IC_{50}$-value determined for native folic acid (~0.9 nM) which indicates largely retained binding affinity of the folic acid derivative 3'-aza-2'-fluorofolic acid.

Example 11: Biodistribution Studies

In vivo experiments were approved by the local veterinarian department and conducted in accordance to the Swiss law of animal protection. Six to eight-week-old female, athymic nude mice (CD-1 Foxn-1/nu) were purchased from Charles River Laboratories (Sulzfeld, Germany). The animals were fed with a folate-deficient rodent diet starting 5 days prior to the tumor cell inoculation. Mice were inoculated with KB cells ($5 \times 10^6$ cells in 100 L PBS) into the subcutis of each shoulder. Animal experiments were performed approximately 14 days after tumor cell inoculation. Biodistribution studies were performed in triplicate. [$^{18}$F]-3'-aza-2'-fluorofolic acid was diluted in PBS pH 7.4 to the desired radioactivity concentration (~5 MBq per mouse) for immediate administration via a lateral tail vein. Blocking studies were performed by injection of excess folic acid (100 g in 100 L PBS) immediately before administration of 3'-aza-2'-[$^{18}$F]fluorofolic acid.

The animals were sacrificed at 30 min, 60 min and 190 min after administration of the radiofolate 3'-aza-2'-[$^{18}$F] fluorofolic acid. Selected tissues and organs were collected, weighed, and counted for radioactivity in a –counter. The results were listed as percentage of the injected dose per gram of tissue weight [% ID/g], using reference counts from a definite sample of the original injectate that was counted at the same time.

The obtained are summarized in Table 2 and represent the percentage injected dose per gram tissue [% ID/g] averaged from three or four animals (Table 2).

TABLE 2

Biodistribution data of [$^{18}$F]-3'-aza-2'-fluorofolic acid ([$^{18}$F]-3) in nude mice bearing KB tumor xenografts

| Organ or tissue | 30 min p.i. (n = 4) | 60 min p.i. (n = 4) | 90 min p.i. (n = 4) | 60 min p.i. blockade* (n = 3) |
|---|---|---|---|---|
| % ID/g in: | | | | |
| Blood | 1.2 ± 0.3 | 0.6 ± 0.1 | 0.6 ± 0.1 | 0.8 ± 0.3 |
| Heart | 2.1 ± 0.2 | 1.9 ± 0.3 | 1.8 ± 0.1 | 0.4 ± 0.2 |
| Lungs | 2.0 ± 0.3 | 1.5 ± 0.2 | 1.6 ± 0.3 | 0.7 ± 0.3 |
| Spleen | 1.3 ± 0.2 | 1.9 ± 0.1 | 2.2 ± 0.2 | 0.4 ± 0.2 |
| Liver | 13.7 ± 2.9 | 10.6 ± 0.9 | 10.3 ± 2.4 | 10.9 ± 3.4 |
| Gallbladder | 8.1 ± 2.9 | 8.4 ± 1.8 | 9.3 ± 0.6 | 15.8 ± 9.3 |
| Kidneys | 54.8 ± 6.1 | 53.6 ± 3.2 | 57.3 ± 8.4 | 5.9 ± 4.5 |
| Stomach | 2.8 ± 0.5 | 2.8 ± 0.9 | 2.7 ± 0.1 | 0.6 ± 0.3 |
| Intestine | 1.4 ± 0.1 | 1.9 ± 0.2 | 2.3 ± 0.4 | 1.3 ± 0.6 |
| Feces | 1.2 ± 0.2 | 3.0 ± 2.0 | 1.8 ± 0.3 | 6.0 ± 1.1 |
| Salivary glands | 9.0 ± 1.3 | 15.0 ± 6.1 | 14.1 ± 0.9 | 0.6 ± 0.2 |
| Bone | 2.1 ± 0.3 | 1.6 ± 0.3 | 1.6 ± 0.3 | 0.6 ± 0.3 |
| Muscle | 1.7 ± 0.4 | 1.2 ± 0.2 | 1.5 ± 0.4 | 0.3 ± 0.1 |
| Tumor | 11.7 ± 0.9 | 11.9 ± 1.7 | 12.6 ± 1.8 | 1.7 ± 0.4 |
| Ratios: | | | | |
| Tumor/Liver | 0.9 ± 0.2 | 1.1 ± 0.2 | 1.3 ± 0.4 | 0.2 ± 0.1 |
| Tumor/Kidneys | 0.2 ± 0.1 | 0.2 ± 0.1 | 0.2 ± 0.1 | 0.4 ± 0.2 |
| Tumor/Blood | 11.1 ± 4.1 | 21.6 ± 2.3 | 23.8 ± 4.1 | 2.2 ± 0.3 |

*In the blockade group, each animal received 100 µg of folic acid in PBS 10 min before radiotracer injection.

Example 12: PET Imaging Studies

PET experiments were performed with an eXplore VISTA PET/CT tomograph (GE). Tumor bearing mice were injected with 10-18 MBq of 3'-aza-2'-[$^{18}$F]fluorofolic acid (100-150 µl per injection) via lateral tail vein. For blocking studies, the animals received excess folic acid (100 µg in 100 µl) via intravenous injection 10 min prior to the radiotracer injection. Animals were anesthetized with isoflurane in an air/oxygen mixture. The PET scans were acquired from 120-150 min p.i. After acquisition, PET data were reconstructed in user-defined time frames. The fused datasets of PET and CT were analyzed with PMOD (version 3.2) software.

Figure 6:
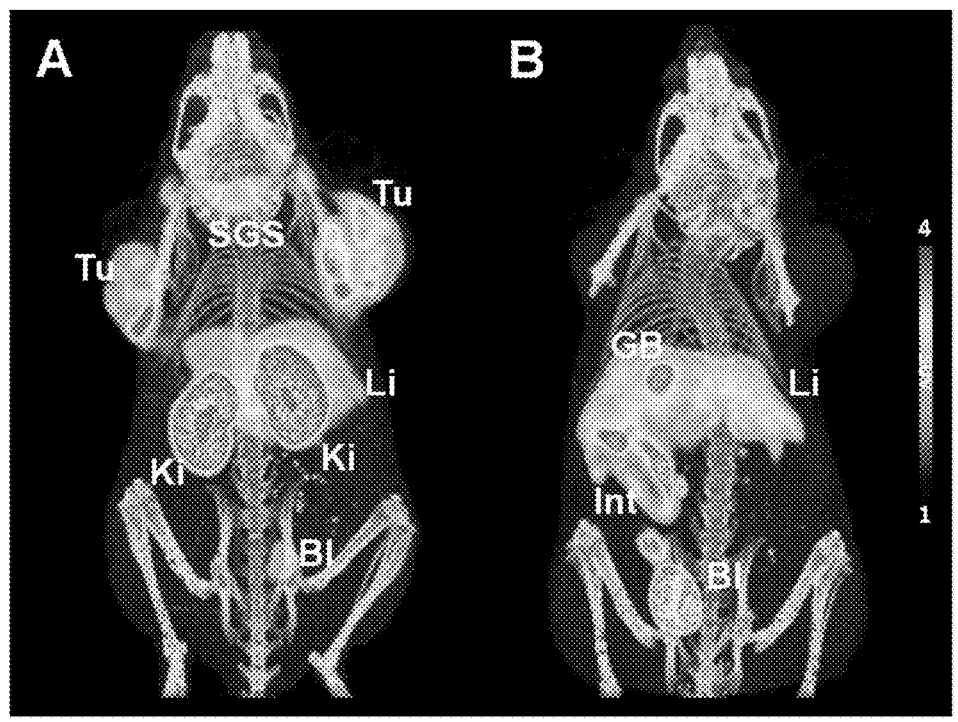
FIG. 6. PET-images (maximal intensity projection) of KB tumor-bearing mice 120-150 min after injection of 3'-aza-2'-[$^{18}$F]fluorofolic acid alone (A) and after injection of excess folic acid and [$^{18}$F]-3'-aza-folic acid (B).
Figure 7:
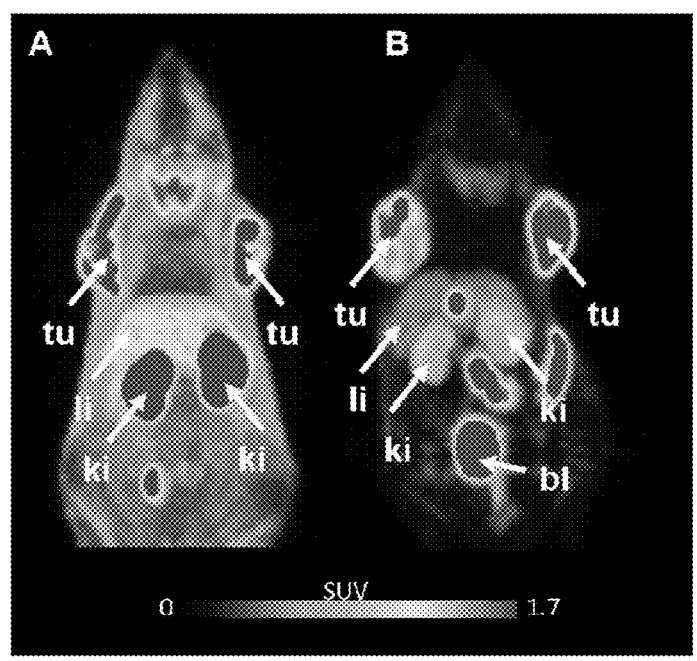
FIG. 7. PET-images (maximal intensity projection) of KB tumor-bearing mice 120-150 min after injection of 3'-aza-2'-[$^{18}$F]fluorofolic acid alone (A) and in combination with preinjected pemetrexed (B).

Dynamic PET scans of mice 1.5-90 min p.i. of 3'-aza-2'-[$^{18}$F]fluorofolic acid and at 60-150 min p.i. were performed. Static PET scans of [$^{18}$F]-2'3'-aza-folic acid were typically performed with a scan time from 120-150 min p.i. Exemplary results are shown in FIGS. 6A/B and 7. The static baseline scan (120-150 min p.i.) showed a high (SUV 1.9) and specific uptake (12.6±1.8% ID/g) in KB tumor xenografts (FIGS. 6A and 7A). The uptake in other non-target organs was negligible, the only exceptions being the liver, kidneys and salivary glands. The studies performed with coinjected folic acid (120-150 min p.i.) showed a reduced uptake of the radiotracer in the tumor tissue and in the kidneys (FIG. 6B).

Preinjection of pemetrexed (400 µg, 60 min prior to the radiotracer) in PBS (100 µl) showed a reduced kidney uptake of the radiotracer and a very strong reduction of the accumulation in the liver, retaining a high tumor uptake (FIG. 7B).

The invention claimed is:

1. A compound having one of the following formulas IVa, IVb, Va, Vb, Vc or Vd,

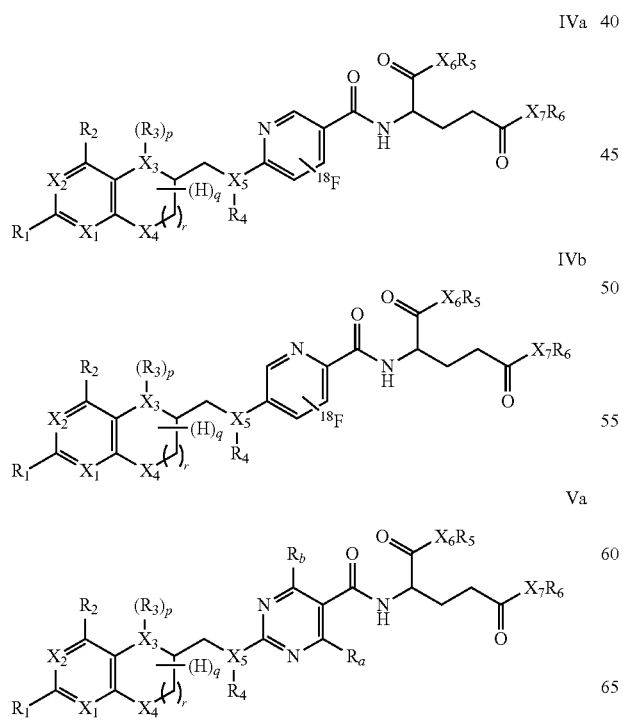
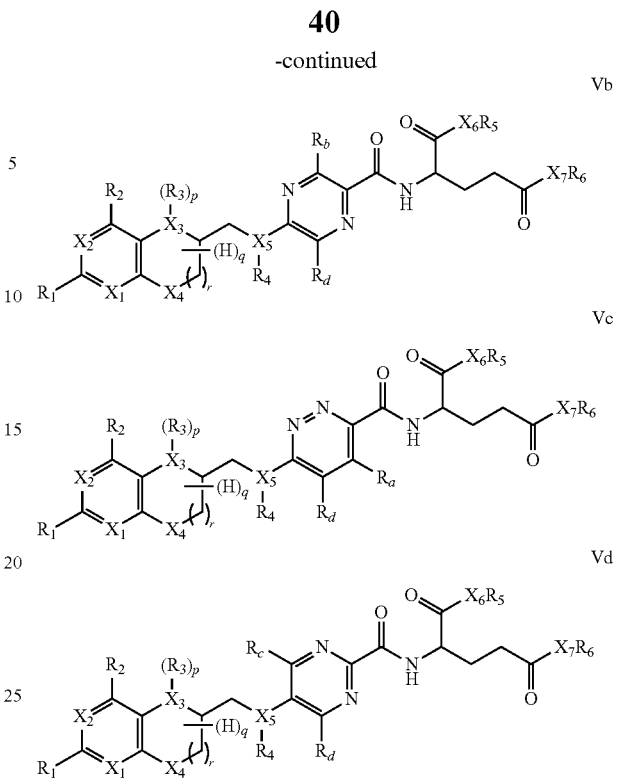

wherein $X_1$ to $X_5$ are independently of each other N or C, $X_6$, $X_7$ are independently of each other C, N or O, $R_a$, $R_b$, $R_c$, $R_d$ are independently of each other H or $^{18}$F, with the proviso that one of $R_a$, $R_b$, $R_c$, $R_d$ is $^{18}$F, $R_1$, $R_2$ are independently of each other H, Hal, —$OR_7$, —$NR_8R_9$, C1-C12 alkyl, C1-C12 alkoxy, C1-C12 alkanoyl, C2-C12 alkenyl, C2-C12 alkynyl, (C1-C12 alkoxy)carbonyl, or (C1-C12 alkylamino)carbonyl, wherein $R_7$ is H or C1-C6 alkyl and $R_8$, $R_9$ are independently of each other H, formyl, or straight chain or branched C1-C12 alkyl, which is unsubstituted or substituted by at least one CN, Hal or $NO_2$, and wherein one or more of embedded, non-adjacent $CH_2$ groups are optionally independently replaced by —O—, —CO—, —CO—O—, —CO—NR'—, —CH=CH—, or —C≡C—, wherein R' is H or C1-C6 alkyl, $R_3$, $R_4$ are independently of each other H, formyl, iminomethyl, nitroso, C1-C12 alkyl, C1-C12 alkoxy, C1-C12 alkanoyl, or halosubstituted C1-C12 alkanoyl, $R_5$, $R_6$ are independently of each other H or straight chain or branched C1-C12 alkyl, which is unsubstituted or substituted by at least one CN, Hal, or $NO_2$, and wherein one or more of embedded, non-adjacent $CH_2$ groups are optionally independently replaced by —O—, —CO—, —CO—O—, —CO—NR'—, —CH=CH—, or —C≡C—, wherein R' is H or C1-C6 alkyl, p is 0, 1 or 2, q has a value of 1 to 7, and r is 1, or a pharmaceutically acceptable salt thereof.

2. The compound according to claim 1, having one of formulas IVc, IVd or IVe,

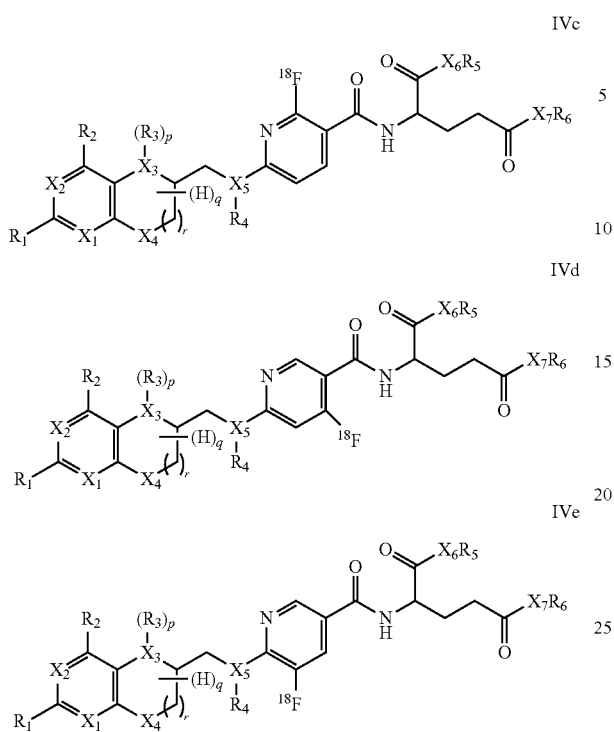

IVc

IVd

IVe wherein $X_1$ to $X_5$ are independently of each other N or C, $X_6$, $X_7$ are independently of each other C, N or O, $R_1$, $R_2$ are independently of each other H, Hal, —$OR_7$—$NR_8R_9$, C1-C12 alkyl, C1-C12 alkoxy, C1-C12 alkanoyl, C2-C12 alkenyl, C2-C12 alkynyl, (C1-C12 alkoxy)carbonyl, or (C1-C12 alkylamino)carbonyl, wherein $R_7$ is H or C1-C6 alkyl and $R_8$, $R_9$ are independently of each other H, formyl, or straight chain or branched C1-C12 alkyl, which is unsubstituted or substituted by at least one CN, Hal or $NO_2$, and wherein one or more of embedded, non-adjacent $CH_2$ groups are optionally independently replaced by —O—, —CO—, —CO—O—, —CO—NR'—, —CH=CH—, or —C≡C—, wherein R' is H or C1-C6 alkyl, $R_3$, $R_4$ are independently of each other H, formyl, iminomethyl, nitroso, C1-C12 alkyl, C1-C12 alkoxy, C1-C12 alkanoyl, or halosubstituted C1-C12 alkanoyl, $R_5$, $R_6$ are independently of each other H or straight chain or branched C1-C12 alkyl, which is unsubstituted or substituted by at least one CN, Hal, or $NO_2$, and wherein one or more of embedded, non-adjacent $CH_2$ groups are optionally independently replaced by —O—, —CO—, —CO—O—, —CO—NR'—, —CH=CH—, or —C≡C—, wherein R' is H or C1-C6 alkyl, p is 0, 1 or 2, q has a value of 1 to 7, and r is 1, or a pharmaceutically acceptable salt thereof.

3. The compound according to claim 1, having one of formulas IVf or IVg,

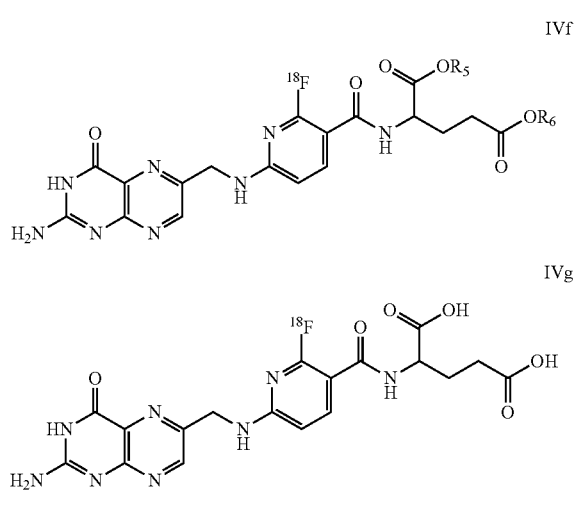

IVf

IVg wherein $R_5$, $R_6$ are independently of each other H or straight chain or branched C1-C12 alkyl, which is unsubstituted or substituted by at least one CN, Hal, or $NO_2$, and wherein one or more of embedded, non-adjacent $CH_2$ groups are optionally independently replaced by —O—, —CO—, —CO—O—, —CO—NR'—, —CH=CH—, or —C≡C—, wherein R' is H or C1-C6 alkyl, or a pharmaceutically acceptable salt thereof.

4. The compound according to claim 1 having one of formulas IXa, IXb, IXc, IXd, IXe or IXf

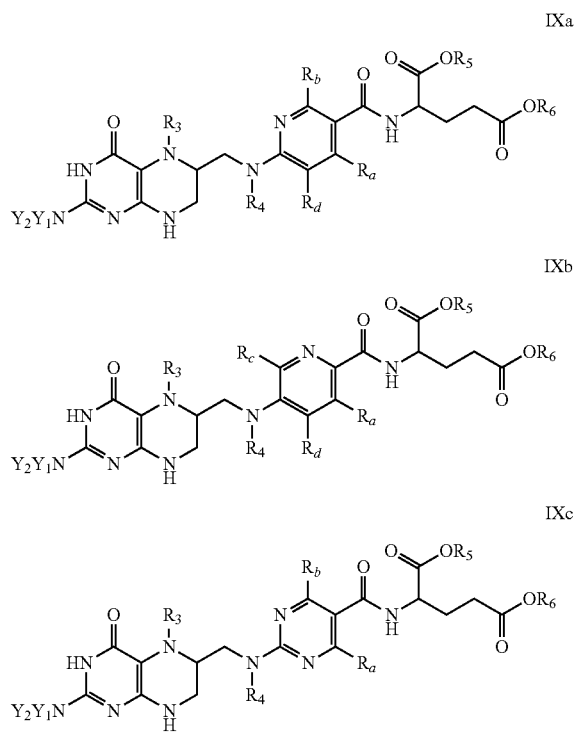

IXa

IXb

IXc

-continued

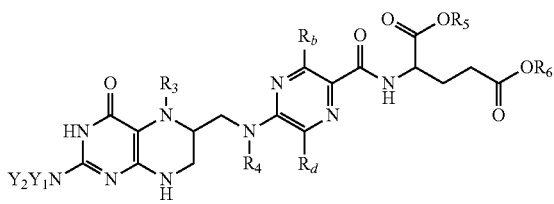
IXd

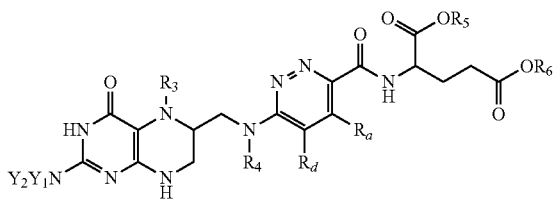
IXe

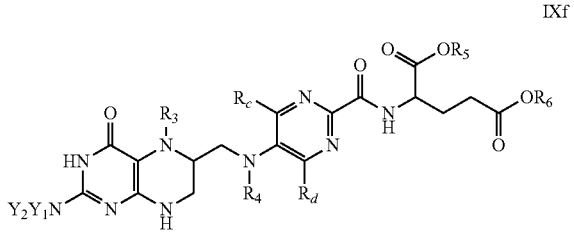
IXf wherein
- $R_a$, $R_b$, $R_c$, $R_d$ are independently of each other $^{18}F$ or H, with the proviso that one of $R_a$, $R_b$, $R_c$, $R_d$ is $^{18}F$,
- $R_3$, $R_4$ are independently of each other H, formyl, iminomethyl, nitroso, C1-C12 alkyl, C1-C12 alkoxy, C1-C12 alkanoyl, or halosubstituted C1-C12 alkanoyl,
- $R_5$, $R_6$ are independently of each other H or straight chain or branched C1-C12 alkyl, which is unsubstituted or substituted by at least one CN, Hal, or $NO_2$, and wherein one or more of embedded, non-adjacent $CH_2$ groups are optionally independently replaced by —O—, —CO—, —CO—O—, —CO—NR'—, —CH=CH— or —C≡C—, wherein R' is H or C1-C6 alkyl,
- $Y_1$, $Y_2$ are independently of each other H, formyl, or a straight chain or branched $C_1$-$C_{12}$ alkyl, which is unsubstituted or substituted by at least one CN, Hal, or $NO_2$ and wherein one or more of embedded, non-adjacent $CH_2$ groups are optionally independently replaced by —O—, —CO—, —CO—O—, —CO—NR'—, —CH=CH—, or —C≡C—, wherein R' is H or C1-C6 alkyl, or a pharmaceutically acceptable salt thereof.

5. The compound of claim 1 having one of formulas XIIa, XIIb, XIIc, XIId, XIIe or XIIf XIIa

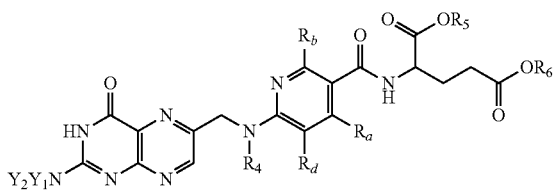

XIIb

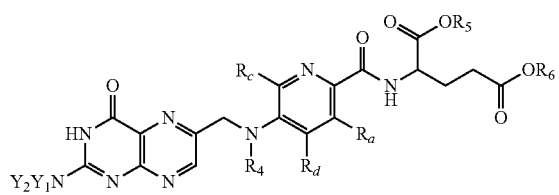

XIIc

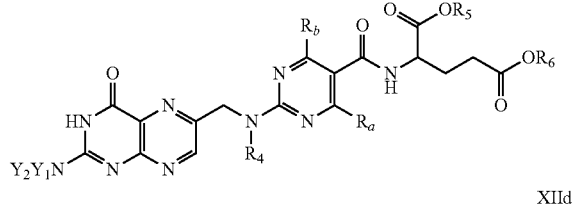

XIId

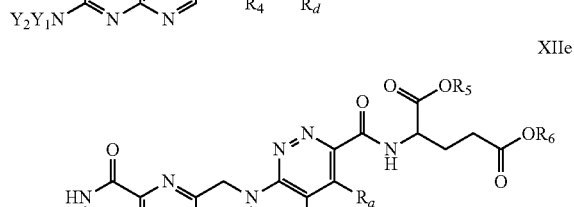

XIIe

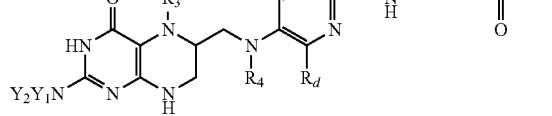

XIIf

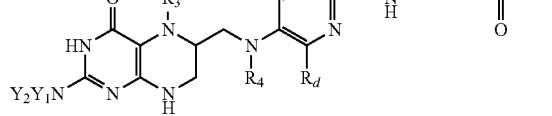

wherein
- $R_a$, $R_b$, $R_c$, $R_d$ are independently of each other $^{18}F$ or H, with the proviso that one of $R_a$, $R_b$, $R_c$, $R_d$ is $^{18}F$,
- $R_4$ is H, formyl, iminomethyl, nitroso, C1-C12 alkyl, C1-C12 alkoxy, C1-C12 alkanoyl, or halosubstituted C1-C12 alkanoyl,
- $R_5$, $R_6$ are independently of each other H or straight chain or branched C1-C12 alkyl, which is unsubstituted or substituted by at least one CN, Hal, or $NO_2$, and wherein one or more of embedded, non-adjacent $CH_2$ groups are optionally independently replaced by —O—, —CO—, —CO—O—, —CO—NR'—, —CH=CH—, or —C≡C—, wherein R' is H or C1-C6 alkyl,
- $Y_1$, $Y_2$ are independently of each other H, formyl, or a straight chain or branched $C_1$-$C_{12}$ alkyl, which is unsubstituted or substituted by at least one CN, Hal, or $NO_2$ and wherein one or more of embedded, non-adjacent $CH_2$ groups are optionally independently replaced by —O—, —CO—, —CO—O—, —CO—NR'—, —CH=CH—, or —C≡C—, wherein R' is H or C1-C6 alkyl, or a pharmaceutically acceptable salt thereof.

6. The compound of claim 1 having one of formulas XVa, XVb, XVc, XVd, XVe or XVf

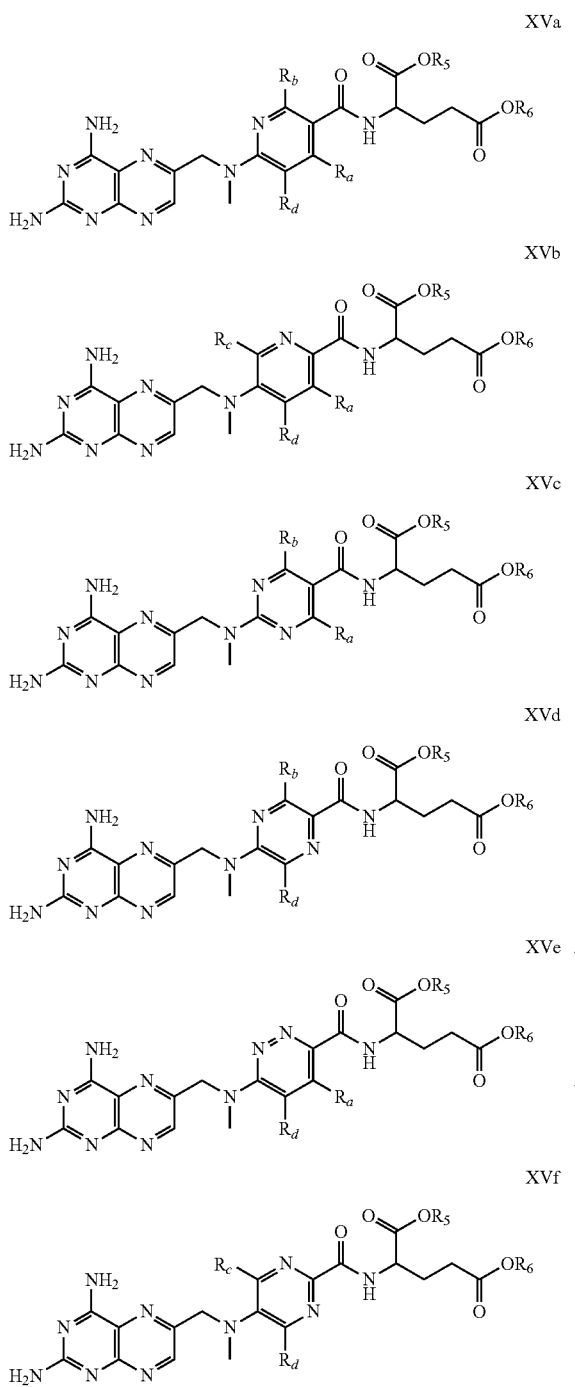

wherein $R_a$, $R_b$, $R_c$, $R_d$ are independently of each other $^{18}F$ or H, with the proviso that one of $R_a$, $R_b$, $R_c$, $R_d$ is $^{18}F$, $R_5$, $R_6$ are independently of each other H or straight chain or branched C1-C12 alkyl, which is unsubstituted or substituted by at least one CN, Hal, or $NO_2$, and wherein one or more of embedded, non-adjacent $CH_2$ groups are optionally independently replaced by —O—, —CO—, —CO—O—, —CO—NR'—, —CH=CH—, or —C≡C—, wherein R' is H or C1-C6 alkyl, or a pharmaceutically acceptable salt thereof.

7. A method of production of a compound according to claim 1 comprising providing a precursor which is a azafolate carrying a substituent amenable to substitution by a [$^{18}F$]fluoride, and reacting said precursor with the [$^{18}F$] fluoride.

8. A method for diagnostic imaging of a cell or population of cells expressing a folate-receptor, said method comprising administering at least one compound according to claim 1 in a diagnostic imaging amount, and obtaining a diagnostic image of said cell or population of cells.

9. The method according to claim 8, wherein the diagnostic imaging is performed on a cell or population of cells expressing a folate-receptor in vitro or in vivo.

10. A method for in vitro detection of a cell expressing the folate receptor in a tissue sample which includes contacting said tissue sample with a compound according to claim 1 in an effective amount and for sufficient time to allow binding to occur and detecting such binding.

11. A method of diagnostic imaging or monitoring a subject comprising the steps of (i) administering at least one compound according to claim 1 in a diagnostic imaging amount, and (ii) performing diagnostic imaging using PET by detecting a signal from said at least one compound.

12. A method of monitoring cancer or inflammatory and autoimmune disease therapy in a subject comprising (i) administering to a subject in need thereof at least one compound according to claim 1 in a diagnostic imaging amount in combination with a further therapeutically active compound, and (ii) performing diagnostic imaging using PET by detecting a signal from said at least one compound to follow the course of cancer or inflammatory and autoimmune disease therapy.

13. The method of claim 11, which is used in combination with any method of diagnosis or therapy of cancer or inflammatory and autoimmune disease.

* * * * *

UNITED STATES PATENT AND TRADEMARK OFFICE
CERTIFICATE OF CORRECTION

PATENT NO. : 10,357,576 B2
APPLICATION NO. : 14/399688
DATED : July 23, 2019
INVENTOR(S) : Roger Schibli et al.

Page 1 of 1

It is certified that error appears in the above-identified patent and that said Letters Patent is hereby corrected as shown below:

On the Title Page

Item (73) Assignee:
Reads: -- MERECK & CIE, Schaffhusen (CH) --.
Should read: -- MERCK & CIE, Schaffhausen (CH) --.

Signed and Sealed this
Twenty-sixth Day of November, 2019

Andrei Iancu
*Director of the United States Patent and Trademark Office*